United States Patent [19]

Ben-Haim et al.

[11] Patent Number: 5,718,241
[45] Date of Patent: Feb. 17, 1998

[54] APPARATUS AND METHOD FOR TREATING CARDIAC ARRHYTHMIAS WITH NO DISCRETE TARGET

[75] Inventors: Shlomo Ben-Haim; Susan J. Zachman, both of Haifa, Israel

[73] Assignee: Biosense, Inc., Orangeburg, N.Y.

[21] Appl. No.: 476,200

[22] Filed: Jun. 7, 1995

[51] Int. Cl.$^6$ ............................................. A61B 5/04
[52] U.S. Cl. ............................ 128/702; 128/705
[58] Field of Search ........................ 128/642, 702, 128/705; 607/122

[56] References Cited

U.S. PATENT DOCUMENTS

| | | |
|---|---|---|
| 4,173,228 | 11/1979 | Van Steenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,940,064 | 7/1990 | Desai . |
| 4,945,305 | 7/1990 | Blood . |
| 5,000,190 | 3/1991 | Petre . |
| 5,012,814 | 5/1991 | Mills et al. . |
| 5,025,786 | 6/1991 | Siegel . |
| 5,041,973 | 8/1991 | Lebron et al. . |
| 5,042,486 | 8/1991 | Pfeiler et al. . |
| 5,054,492 | 10/1991 | Scribner . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. ............................ 128/786 |
| 5,246,016 | 9/1993 | Lieber et al. . |
| 5,295,484 | 3/1994 | Marcus et al. . |
| 5,297,549 | 3/1994 | Beatty et al. . |
| 5,311,873 | 5/1994 | Savard . |
| 5,335,663 | 8/1994 | Oakley . |
| 5,341,807 | 8/1994 | Nardella . |
| 5,391,199 | 2/1995 | Ben-Haim . |
| 5,433,198 | 7/1995 | Desai ................................... 128/642 |
| 5,487,385 | 1/1996 | Avitall ................................... 128/642 |
| 5,487,391 | 1/1996 | Panescu ................................ 128/642 |
| 5,582,609 | 12/1996 | Swanson et al. ...................... 128/642 |

FOREIGN PATENT DOCUMENTS

| | | |
|---|---|---|
| 0499491 | 8/1992 | European Pat. Off. . |
| 9406349 | 3/1994 | WIPO ................................... 128/642 |

OTHER PUBLICATIONS

William, J.M., et al., Left Atrial Isolation: A New Technique for the Treatemnt for Supreventricular Arrhythmias, *Journal of Thoracic Cardiovascular Surgery*, 1980 (vol. 80), pp. 373–380.

(List continued on next page.)

*Primary Examiner*—Marvin M. Lateef
*Assistant Examiner*—Carl H. Layno
*Attorney, Agent, or Firm*—Cowan, Liebowitz & Latman, P.C.; William H. Dippert

[57] ABSTRACT

A method and apparatus for treating cardiac arrhythmias with no discrete focus. More particularly, one or more catheters are used to collect local information concerning a patient's heart, the information is analyzed to determine where lines or points of ablation should be made, and then the lines or points of ablation are made.

87 Claims, 16 Drawing Sheets

OTHER PUBLICATIONS

Guiraudon, G.N., et al., Combined Sino–atrial Node Ventricular Node Isolation: A Surgical Alternative to AV Node Ablation in Patients with Atrial Fibrillation (abstract), *Circulation*, 1985 (72), pp. 111–220.

Swartz, J.F., Pellersels, G., Silvers, J., Patten, L., and Cervantez, D., A Catheter Based Curative Approach to Atrial Fibrillation in Humans (abstract), Circulation, 1994(90,4), Part 2, p. I-335.

Seifert, M.J., Friedman, M.F., Selke, F.W., and Josephson, M.E., Radiofrequency Maze Ablation for Atrial Fibrillation (abstract), *Circulation*, 1994 (90,4), Part 2, p. I-595.

Haines, D.E., McRury, I.A., Whayne, J.G., and Fleischman, S.D., Atrial Radiofrequency Ablation: The Use of a Novel Deploying Loop Catheter Design to Create Long Linear Lesions (abstract), *Circulation*, 1994, (90, 4), Part 2, p. I-335.

Josephson et al., Role of Catheter Mapping in the Preoperative Evaluation of Ventricular Tachycardia, *The American Journal Of Cardiology*, vol. 40, pp. 207–220, Jan. 1982.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Activation During Ventricular Endocardial Pacing—II: Role of Pace–Mapping to Localize Origin of Ventricular Tachycardia *The American Journal Of Cardiology*, vol. 30, 50, pp. 11–22, Jul. 1982.

Witnowski et al., An Automated Simultaneous Transmural Cardiac Mapping System, *American Journal Of Physiology* vol. 247, pp. H661-H668, 1984.

Fann et al., Endocardial Activation mapping and Endocardial Pace–Mapping Using a Balloon Apparatus, *American Journal Of Cardiology* vol. 55, pp. 1076–1083, Apr. 1, 1985.

Hauer et al., Endocardial Catheter Mapping: Wire Skeleton Techniques for Representation of Computed Arrhythmogenic Sites Compared with Intraoperative Mapping, *Circulation*, vol. 74, No. 6, pp. 1346–1354, Dec. 1986.

Pogwizd et al., Reentrant and Nonreentrant mechanisms Contribute to Arrhythmogenesis During Early Myocardial Ischemia: Results using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *PACE* vol. 11, pp. 449–459, Apr. 1988.

Jackman et al., New Catheter Technique for Recording Left Free–Wall Accessory Atrioventricular Pathway Activation, *Circulation* vol. 78, No. 3, pp. 598–611, Sep. 1988.

Pagé, Surgical Treatment of Ventricular Tachycardia: Regional Cryoablation Guided by Computerized Epicardial and Endocardial Mapping, *Circulation* vol. 80, (Supplement I), No. 3, pp. I-124 –I-134, Sep. 1989.

Tweddel et al., Potential Mapping in Septal Tachycardia: Evaluation of a New Intraoperative Mapping Technique, *Circulation* vol. 80, (Supplement I), No. 3, pp. I-97 –I-108, Sep. 1989.

Shenasa et al., Cardiac Mapping. Part I: Wolff–Parkinson–White Syndrome *PACE*, vol. 13, pp. 223–230, Feb. 1990.

Scheinman et al., Current Role of Catheter Ablative Procedures in Patients with Cardiac Arrhythmias, *Circulation* vol. 83, No. 6, pp. 2146–2153, Jun. 1991.

Buckles et al., Computer–Enhanced Mapping of Activation Sequences in the Surgical Treatment of Supraventricular Arrhythmias, *PACE* vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, Journal of American College Of Cardiologists vol. 17, No. 2, pp. 403–408, Feb. 1991.

Kaltenbrunner et al., Epicardial and Endocardial Mapping of Ventricular Tachycardia in Patients with Myocardial Infarction, *Circulation* vol. 83, No. 3, pp. 1058–1071, Sep. 1991.

Massé et al., A Three–Dimensional Display for Cardiac Activation Mapping, *PACE*, vol. 14, Pt. 1, pp. 538–545, Apr. 1991.

Desai et al., Orthogonal Electrode Catheter Array for Mapping of Endocardial Focal Site of Ventricular Activation, *PACE* vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *PACE* vol. 15, pp. 854–858, Jun. 1992.

Chen et al., Reappraisal of Electrical Cure of Atrioventricular Nodal Reentrant Tachycardia –Lesions from a Modified Catheter Ablation Technique *INTERNATIONAL JOURNAL OF CARDIOLOGY*, vol. 37, pp. 51–60, 1992.

Chen et al., Radiofrequency Catheter Ablation for Treatment of Wolff–Parkinson–White Syndrom –Short–and Long–term Follow–up *INTERNATIONAL JOURNAL OF CARDIOLOGY*, vol. 37, pp. 199–207, 1992.

Scheinman, North American Society of Pacing and Electrophysiology (NASPE) Survey of Radiofrequency Catheter Ablation: Implications for Clinicians, Third Party Insurers, and Government Regulatory Agencies, *PACE* vol. 15, pp. 2228–2231, Dec. 1992.

Silka et al., Phase Image Analysis of Anomalous Ventricular Activation in Pediatric Patients with Preexcitation Syndromes or Ventricular Tachycardia, *AMERICAN HEART JOURNAL* vol. 125, No. 2, Pt. 1, pp. 372–380, Feb. 1993.

Josephson, Clinical Cardiac Electrophysiology: Techniques and Interpretations, 2nd Ed. pp. 566–580, 608–615, 770–783, Lea & Febiger, Malvern Pa., 1993.

Kuchar et al., Electrocardiographic Localization of the Site of Ventricular Tachycardia in Patients with Prior Myocardial Infarction, *JACC*, vol. 13, No. 4, pp. 893–900, 1989.

Holt et al., Ventricular Arrhythmias –A Guide to Their Localization, *BRITISH HEART JOURNAL*, vol. 53, pp. 417, 430, 1985.

Wolf, P.A., Dawber, T.R., Thomas, H.E. Jr., Kannel, W.B., Epidemiologic assessment of chronic atrial fibrillation and the risk of stroke: The Framingham Study, *NEUROLOGY*, 1978 (vol. 28), pp. 373–375.

Cox, J.L., Schuessler R.B., Boineau J.B., in Surgery for Atrial Fibrillation, Cardiac Surgery; State of the Art Reviews, 1990 (vol. 4), pp. 207–217.

Williams, J.M., Ungerleider, R.M., Lofmand, J.K., Cox, J.L., Left Atrial Isolation: A New Technique for the Treatment for Supraventricular Arrhythmias, *JOURNAL OF THORACIC CARDIOVASCULAR SURGERY*, 1980 (vol. 80), pp. 373–380.

Guiraudon G.N., Campbell C.S., Jones D.L., McLellan D.G., and MacDonald J.L., Combined Sino–atrial Node Ventricular Node Isolation: A Surgical Alternative to AV Node Ablation in Patients with Atrial Fibrillation (abstract), *CIRCULATION*, 1985(75), p. III–220.

Cox, J.L., Boineau, J.P., Schuessler, R.B., Kater, K.M., and Lappas, D.G., Surgical Interruption of Atrial Reentry as a cure for Atrial Fibrillation, Olsson, S.B., Allessie, M.A., Campbell, R.W.F. (editors), Atrial Fibrillation: Mechanisms and Therapeutic Strategies, Futura Publishing Co., Inc., Armonk, NY, 1994.

Swartz, J.F, Pellersels, G., Silvers, J., Patten, L., and Cervantez, D., A Catheter Based Curative Approach to Atrial Fibrillation in Humans (abstract), *CIRCULATION*, 1994(90, 4), Part 2, p. I–335.

APPARATUS AND METHOD FOR TREATING CARDIAC ARRHYTHMIAS WITH NO DISCRETE TARGET

FIELD OF THE INVENTION

This invention is directed to the treatment of cardiac arrhythmias. More particularly, this invention is directed to an apparatus and method for treating cardiac arrhythmias with no detectable anatomical targets, i.e., no fixed aberrant pathways.

BACKGROUND OF THE INVENTION

In the healthy heart, cardiac muscle cells are electrically stimulated to contract in a sequential, synchronized manner, the propagation starting in the sinus node in the right atrium and spreading through the heart as each cell stimulates neighboring cells. The activation of each muscle cell is followed by a period in which the cell is incapable of being stimulated again. This period is called the refractory period, and it functions to ensure a smooth contraction of the muscle and the efficient flow of blood through the chambers of the heart. In a patient with a cardiac arrhythmia, the propagation of the electrical stimulation of the muscle does not proceed as it should. The heart rate may be too fast or too slow, or the electrical stimulation of the heart may progress through an abnormal pathway. The abnormal pathways may be fixed or they may be functional, i.e., with no fixed circuit or focus.

There are several types of cardiac arrhythmias in which the presence of some fixed anatomical defect (such as non-conducting scar tissue left as a result of myocardial infarction) gives rise to the creation of an abnormal electrical pathway that may lead to the development of a sustained arrhythmia that would develop under the proper conditions. Current medical therapy of arrhythmias with fixed pathways includes ablation of the superfluous pathway. Such fixed anatomical pathways are localized using electrophysiological mapping of the cardiac chambers. In the minimally invasive procedures common today, cardiac electrical activation mapping is performed with the aid of x-ray transillumination (fluoroscopy). For identifying the electrical activation sequence of the heart, the local electrical activity is acquired at a site within the patient's heart chamber using a steerable catheter, the position of which is assessed by transillumination images in which the heart chamber is not visible. Local electrical activation time, measured as time elapsed from a common reference event in the cardiac cycle to a fiducial point during the electrical systole, represents the local electrical information needed to construct the activation map data point at a single location. The location of the catheter tip is obtained by an x-ray transillumination that results in a 2-D projection of the catheter within the heart of a patient. Since the heart muscle is translucent to the radiation, the physician can locate a catheter tip position by comparing its shape to a set of known catheter shapes at different positions in the heart (usually after having seen two orthogonal projections).

To generate a complete activation map of the heart, several data points are sampled. The catheter is moved to a different location within the heart chamber and the electrical activation is acquired again, the tip of the catheter is repeatedly portrayed in the transillumination images, and its location is determined.

The activation map generated is used to identify the electrical pathway that is the cause of the patient's arrhythmia. Then, by use of radio frequency (RF) energy delivered through the catheter tip, a discrete lesion is created that disrupts the abnormal pathway. These ablative procedures have proven to be highly successful for treating arrhythmias that can be successfully mapped by this technique, such as accessory atrio ventricular pathways.

In another subset of cardiac arrhythmias, the pathologic mechanism entails emergence of several functional, not anatomically fixed, superfluous electrical pathways. Therefore, ablation of one or more functional pathways in these arrhythmias cannot be curative, as different functional and superfluous pathways would emerge. Currently the treatment of patients suffering from arrhythmias of this category is limited to either anti-arrhythmic medication or implantation of an automatic cardiac defibrillator. In selected cases successful treatment has been achieved by extensive surgical procedures in which the cardiac tissue is remodeled such that the remaining electrically conducting tissue is least likely to support the development or sustainment of cardiac arrhythmias. This approach is associated with high risk for intra-operative mortality.

Atrial fibrillation (AF) is the most common arrhythmia with no anatomically fixed aberrant pathway, and it is a major health care problem. An estimated one million US citizens suffer from atrial fibrillation and are at risk from the effects of the arrhythmia. The most complete epidemiological data compiled on the incidence of atrial fibrillation is the Framingham Heart Study (Wolf, Pa., Dawber, T .R., Thomas, H. E. Jr., Kannel, W. B., Epidemiologic assessment of chronic atrial fibrillation and the risk of stroke: The Framingham study, Neurology, 1978 (Vol. 28), pp 373–375) which demonstrated that more than 5% of healthy people will develop AF after 30 years of follow-up. The incidence of AF in subjects who are in the 25–34 year old age group was 0.2%, and the incidence climbed steadily through the 55–64 year old age group, where it reached 3.8%. Overall, the chance of developing AF in the total population studied was 2.0% over twenty years.

In normal hearts the refractory period of the heart muscle cell is variable with heart rate, and also with its location in the heart chamber, in a manner that facilitates the synchronized contraction of the chamber. In patients with AF, the refractory period of the heart muscle cells may not respond properly to changes in heart rate, and the spatial distribution of refractory periods in the heart chamber may be non-uniform. The substrate of the heart of AF patients also generally exhibits evidence of prolonged conductivity. Under these conditions it becomes possible for functional reentrant electrical pathways to develop. Previous studies have indicated that the product of conduction velocity times atrial refractory period is indicative of the propensity for development of atrial fibrillation.

Although atrial fibrillation is well tolerated by most patients, in some patients the consequences may be severe. Cardiac output may be compromised even at rest, and blood tends to stagnate in the appendages of the fibrillating atria, as a result of which the heart may send emboli to the brain.

Non-surgical Treatment

The most common non-surgical approach to treating atrial fibrillation is to attempt to treat it medically with the use of anti-arrhythmic medications, alone or in conjunction with electrical cardioversion, i.e., electrical defibrillation. The end point of pharmacological therapy tends to be the control of the patient's symptoms. However, some physicians aim to achieve normal sinus rhythm as the end point of the pharmacological therapy. The efficacy of pharmacological therapy has not been demonstrated in large randomized trials. Numerous studies have evaluated the relative efficacy of individual agents; however, no agent has achieved control of atrial fibrillation without the incidence of clinical side effects. Moreover, no agent was able to achieve more than a 40% sustainment of normal sinus rhythm.

Another aspect of non-surgical treatment includes countermeasures to reduce the rate of embolization, such as anti-coagulation therapy. However, in recent years it has become clear that for patient's who have a high risk of embolization such treatment is necessary.

Electrical cardioversion is another way to treat atrial fibrillation by electrically terminating the arrhythmia. Cardioversion involves the delivery of energy to the myocardium, which is synchronized to occur with the QRS complex of the ECG. Cardioversion is the treatment of choice for symptomatic and sudden onset atrial fibrillation, if the patient's clinical condition is stable. Cardioversion may be used as an adjunct to pharmacological therapy, or as a primary means for restoring normal sinus rhythm. It is extremely effective in temporarily interrupting atrial fibrillation, although recurrence rates are quite high. A consideration of treating atrial fibrillation with cardioversion is the possibility of central nervous system thromboembolization during the procedure.

If drug or electrical therapy are not effective in managing the symptomatic atrial fibrillation, a more aggressive treatment, called catheter ablation of the AV junction, may be undertaken. The purpose of such treatment is to permanently block conduction between the atrium and the ventricles. Ventricular rhythm is restored by implanting a permanent ventricular pacemaker. This technique has been successful in controlling supraventricular arrhythmias without the use of adjunct pharmacological agents in more than 75% of patients. However, this therapy causes complete heart block and requires a permanent pacemaker to support ventricular rhythm. The therapy may have detrimental hemodynamic effects in the case of co-existing cardiomyopathy, since the mechanical contribution of the timed atrial contraction is lost. The risk of stroke is still present, and, moreover, complications related to implantation of ventricular pacemakers are now becoming a source of concern.

Surgical Treatment

The first surgical treatment reported for patients with atrial fibrillation was in 1990, by Cox, J. L., Schuessler R. B., Boineau J. B., in Surgery for Atrial Fibrillation, Cardiac Surgery; State of the Art Reviews, 1990 (Vol. 4), pp 207–217. It is also reported in Williams, J. M., Ungerleider, R. M., Lofmand, J. K., Cox, J. L., Left Atrial Isolation: A New Technique for the Treatment for Supraventricular Arrhythmias, Journal of Thoracic Cardiovascular Surgery, 1980 (Vol. 80), pp 373–380. In this report the surgical technique was capable of electrically isolating the majority of the left atrium from the rest of the heart. This procedure was successful in treatment of left atrial focus of atrial fibrillation. However, although sinus rhythm was restored, the mechanical function of the left atrium was not, and the risk of thromboembolism still exists. The corridor procedure for the treatment of atrial fibrillation was reported by Guiraudon G. N., Campbell C. S., Jones D. L., McLellan D. G., and MacDonald J. L., Combined Sino-atrial Node Ventricular Node Isolation: A Surgical Alternative to AV Node Ablation in Patients with Atrial Fibrillation (abstract), Circulation, 1985(72), p III-220. This procedure allows the sinus impulse, originating from the sinus node, to propagate exclusively down a surgically created corridor toward the AV node and then to the ventricles. The segmentation of the atrium does not allow for organized contraction of the atrium and the rest of the atrium may still be in fibrillation, although the heart rate will be restored to its normal sinus rhythm.

In the maze procedure, Cox, J. L., Boineau, J. P., Schuessler, R. B., Kater, K. M., and Lappas, D. G., Surgical Interruption of Atrial Reentry as a Cure for Atrial Fibrillation, Olsson, S. B., Allessie, M. A., Campbell, R. W. F. (editors), Atrial Fibrillation: Mechanisms and Therapeutic Strategies, Futura Publishing Co., Inc., Armonk, N.Y., 1994, after cardiopulmonary bypass is initiated, the heart is arrested with cardioplegic solutions and left and right atrial incisions are performed. Surgical incisions are placed on either side of the sino-atrial node. Surrounding the sino-atrial node with incisions ensures that the sinus impulse can travel in only one direction. Subsequent surgical incisions are then placed so that the impulse can activate both atria and the AV node. As a result of the surgery, the electrical impulse originating from the sinus node is incapable of establishing a reentrant circuit because all the tissue remains refractory after its recent depolarization. By creating a surgical maze of electrical pathways, the atrial tissue can be stimulated, but the substrate necessary to support macro reentry is eliminated.

Both the corridor and the maze procedures as described in the references cited above require major open heart surgery. During the lengthy surgery the patient's circulation must be artificially supported by a heart-lung bypass machine while the electrical activity of both atria are mapped and the atrial incisions are made. Also, these procedures include several right atrial incisions that may interrupt the integrity of the sino-atrial node or its arterial supply, and may require permanent artificial pacing to overcome iatrogenic SA node destruction or blockade. Another complication is the tendency of patients who have undergone the maze procedure to retain fluids. This is associated with damage caused by the surgical incisions to the ability of the right atrium to secrete natriuretic peptides.

Recent work has been reported in which a modification of the maze procedure using RF catheter ablation rather than surgical incisions to create lines of conduction block has been attempted. Swartz, J. F, Pellersels, G., Silvers, J., Patten, L., and Cervantez, D., A Catheter Based Curative Approach to Atrial Fibrillation in Humans (abstract), Circulation, 1994 (90,4), Part 2, p I-335, reported on one patient who was successfully treated by eight lines of ablation delivered to the right and left atria. The ablation lines were delivered by a 7 Fr. catheter with a 4 mm ablation tip using a series of seven anatomically conforming 8 Fr. intravascular introducers. Haines, D. E., McRury, I. A., Whayne, J. G., and Fleischman, S. D., Atrial Radiofrequency Ablation: The Use of a Novel Deploying Loop Catheter Design to Create Long Linear Lesions (abstract), Circulation, 1994, (90,4), Part 2, p I-335, reported on the use of an ablation catheter with an 8 Fr. shaft and two splines at its terminus which form a loop. The report concludes that it is possible to create long linear transmural atrial lesions with this catheter design. Seifert, M. J., Friedman, M. F., Selke, F. W., and Josephson, M. E., Radiofrequency Maze Ablation for Atrial Fibrillation (abstract), Circulation, 1994(90,4), Part 2, p. I-595, report on the epicardial application of RF energy from a custom designed plaque that generates linear lesions. Five swine were studied and the technique showed success in four.

The surgical and non-surgical techniques discussed above each have certain disadvantages. Therefore, there is a strong need for a modality of treating arrhythmias with no discrete target, such as AF, that overcomes or minimizes these disadvantages.

OBJECTS OF THE INVENTION

It is an object of the invention to provide a treatment for cardiac arrhythmias.

It is also an object of the invention to provide an apparatus and a method for the treatment of cardiac arrhythmias that have no fixed aberrant pathways, such as atrial fibrillation.

It is a further object of the invention to provide an apparatus and a method for designing an intervention that will decrease the likelihood of sustainment of cardiac arrhythmias that have no fixed aberrant pathways, such as atrial fibrillation.

These and other objects of the invention will become more apparent in the discussion below.

SUMMARY OF THE INVENTION

The present invention includes means of a locatable, mapping, pacing and ablation catheter tip, and methods for using same for therapy of cardiac arrhythmias with no discrete target. For example, a patient suffering from atrial fibrillation or paroxysmal atrial fibrillation is a candidate for the new mapping and ablation procedure.

According to the invention, a description of the heart chamber anatomy, i.e., the physical dimensions of the chamber, is obtained and an activation map of a patient's heart is created using locatable catheters. A conduction velocity map is derived from the activation map. Then, a refractory period map is acquired. Appropriate values from the conduction velocity map and the refractory period map are used to create a dimension map, which is then analyzed to determine ablation lines or points.

BRIEF DESCRIPTION OF THE DRAWINGS

FIG. 12a shows how placing an ablation line at a distance slightly less than 2a from the edge of the conduction block edge will prevent reentrant pathways from forming alongside the block since the curvature needed to form a circuit would be greater than a;

DETAILED DESCRIPTION OF THE INVENTION

The invention herein concerns an apparatus and a method for treating cardiac arrhythmias with no discrete target, wherein certain information concerning a patient's heart is captured and that information is processed to determine lines or points of ablation. The primary purpose is to eliminate fibrillation. In some cases fibrillation may be minimized in terms of frequency or duration, but not eliminated altogether.

One or more steerable reference and mapping/ablation catheters are used to create an activation map of a heart chamber, and a three-dimensional geometry of the heart chamber is created. Spatial derivation is then performed on the activation map to form a conduction velocity map. Other information sensed in the heart chamber is used to create a refractory period map, and then values from the conduction velocity map and the refractory period map are used to create a dimension map. The dimension map is analyzed to determine lines or points of ablation.

Figure 1:
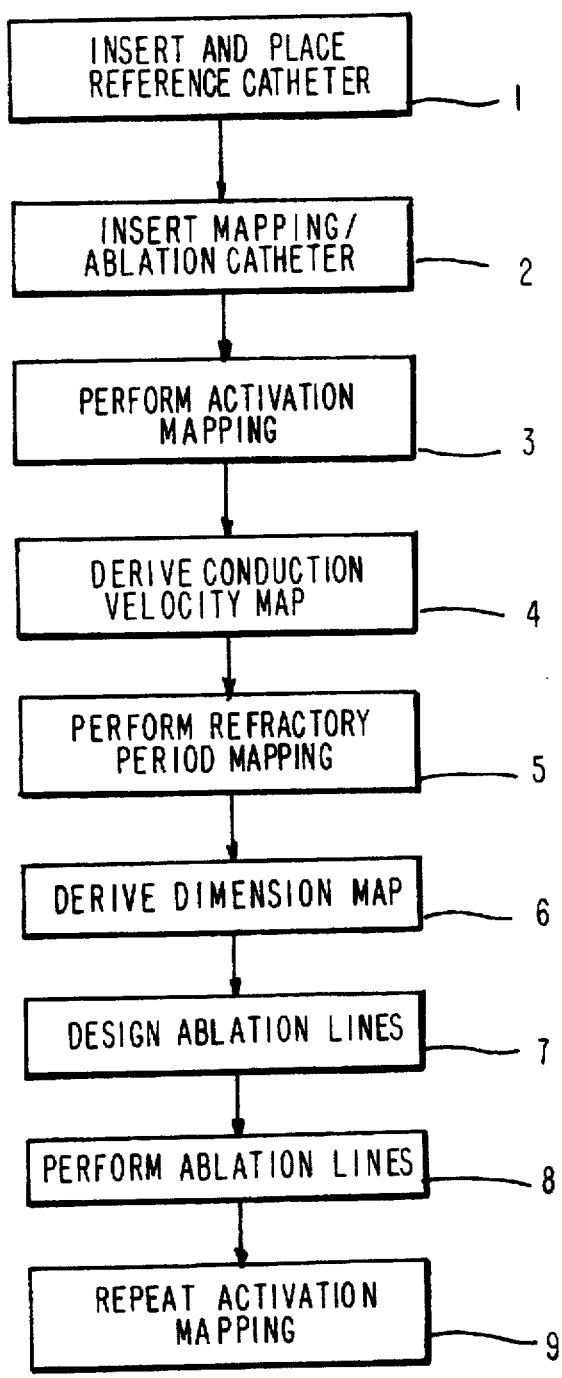
FIG. 1 is a flowchart of an embodiment of the mapping and catheter ablation treatment for atrial fibrillation.
Figure 2:
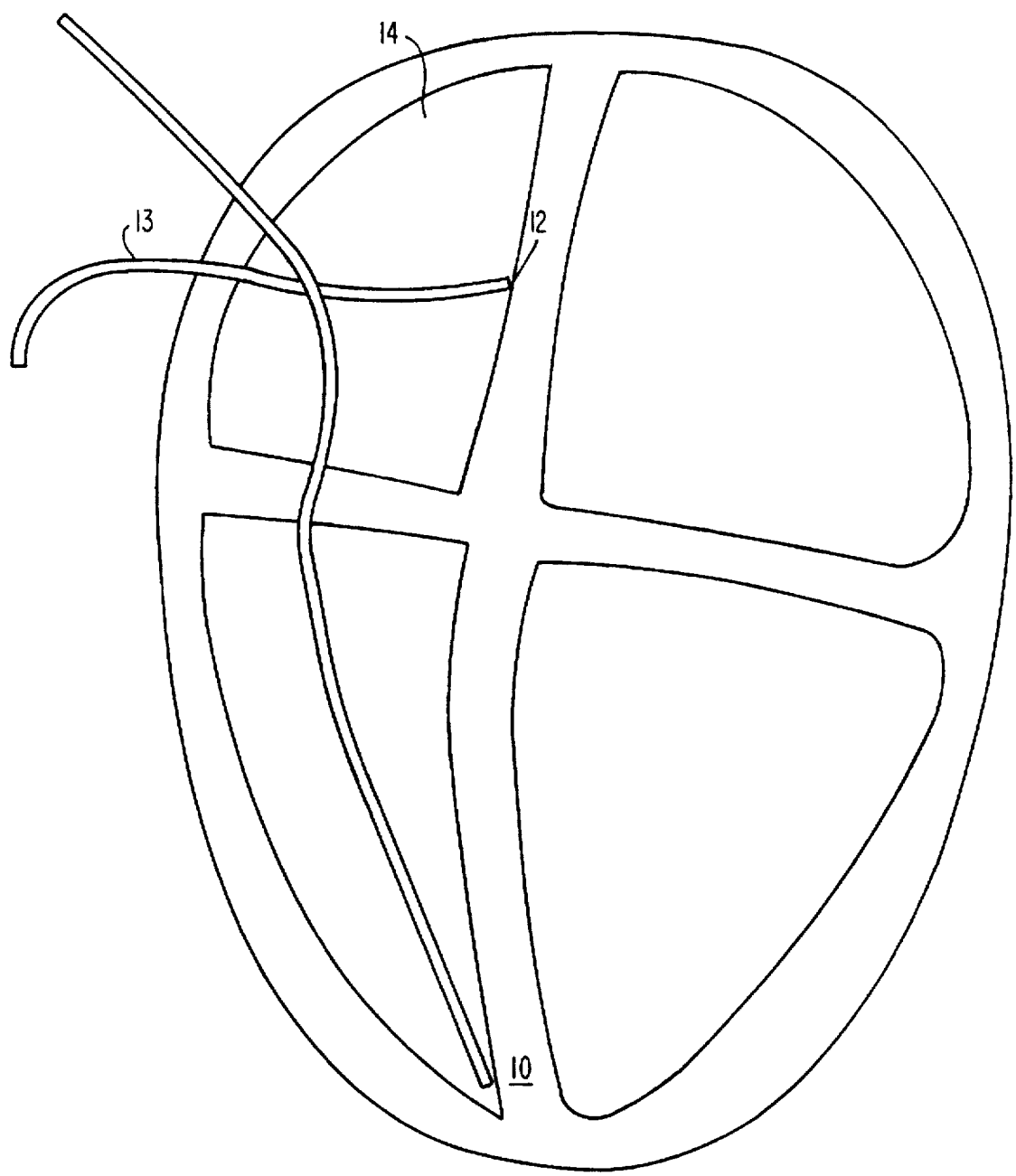
FIG. 2 is a schematic diagram of the heart showing a possible placement of a single reference catheter and the mapping/ablation catheter.

The invention can perhaps be better understood by reference to the drawings. FIG. 1 is a flowchart of an overall method for performing catheter mapping and ablation of atrial fibrillation using the means of a locatable tip mapping and ablation catheter. According to a possible embodiment of the invention, the groin vein is catheterized under local anesthesia and a plurality of catheters are introduced to the heart chamber. Each catheter is locatable at its tip. One or more reference catheters are inserted and placed in stable locations 1, and will remain there for the rest of the mapping and ablation procedure. Possible sights for a single reference catheter are, for example, the coronary sinus or the right ventricular apex (RVA) 10, as shown in FIG. 2. In some possible embodiments, a reference location may be obtained from outside the body, for example, on the patient's skin, and the only catheter inserted into the heart will be the mapping/ablation catheter.

Figure 3:
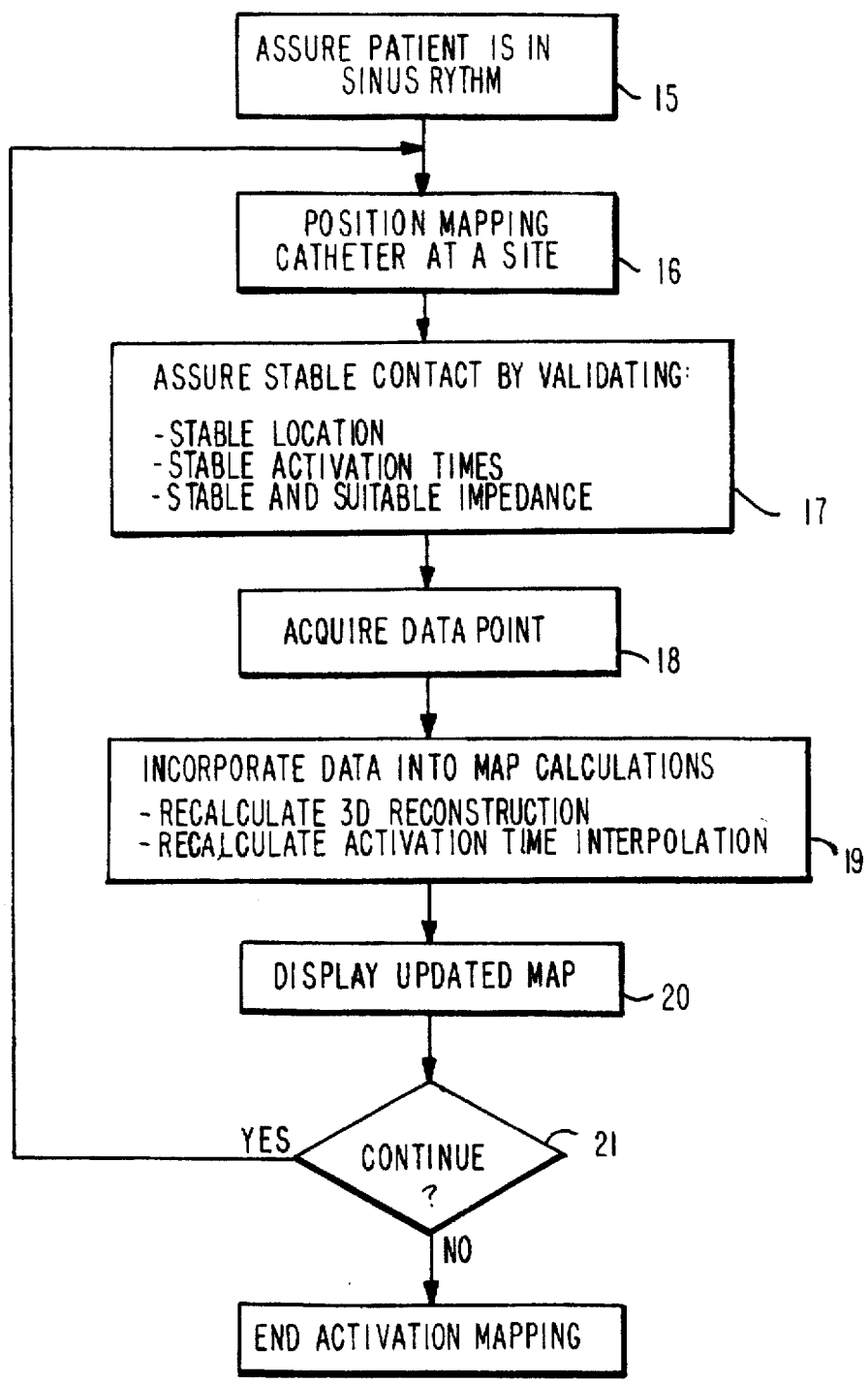
FIG. 3 is a flowchart of the activation mapping procedure.
Figure 4:
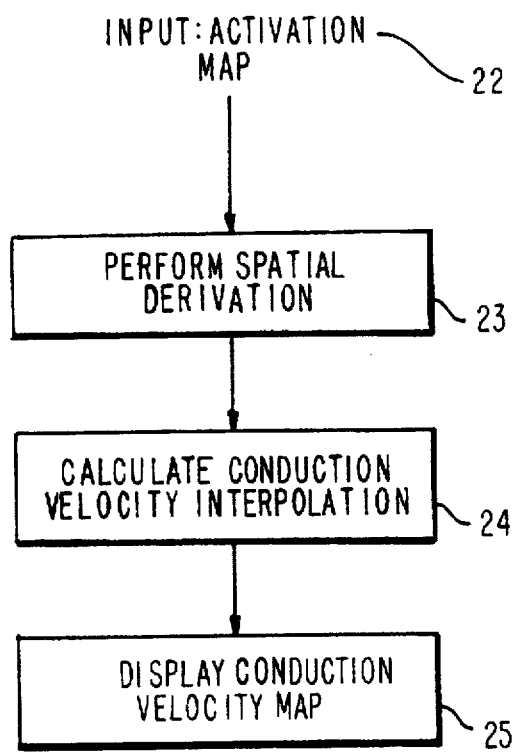
FIG. 4 is a flowchart of the procedure used to derive the conduction velocity map.

An additional catheter, a mapping and ablation catheter 13, is introduced 2 into the right atrium 14. The steps followed in performing activation mapping 3 are outlined in the flowchart of FIG. 3. During the mapping procedure 3, the patient should be in a regular sinus rhythm 15. This can be achieved by cardioverting the patient using an external defibrillator. The location of the mapping catheter 13 relative to the reference catheter 10 is registered continuously using the locating means, as is discussed more fully below. By use of an electrode in or at the tip of the mapping catheter 13, the catheter 13 is placed at a site 12 in the atrium 16. Local activation is recorded only after assuring endocardial contact by, for example, evidence of stable location, stable activation times, and stable and suitable recordings of the local impedance to induced low amplitude, non-stimulating, electrical current (e.g., low current RF source) 17. Local electrical activity is then acquired and the local activation time relative to a fiducial point in the body surface QRS complex is recorded 18.

The activation map is updated after the acquisition of each data point 19, and the information acquired (location and local activation time) is portrayed as the activation map of the atrium under study 20. At the same time, the locations of anatomical obstacles to propagation of electrical activation (conduction blocks such as the entry of veins, ligaments, etc.) are recorded as locations that are not associated with local electrical activity, as evidenced by lack of endocardial contact. More data points are acquired until an activation map superimposed on a reconstruction of the chamber anatomy is sufficiently detailed 21.

A conduction velocity map is derived from the activation map created. In a preferred embodiment, spatial derivation 23 and appropriate interpolation 24 are performed on the activation map 22 to form the conduction velocity map 25. The conduction velocity map 25 can be displayed separately or superimposed on a representation of the chamber anatomy.

Figure 5:
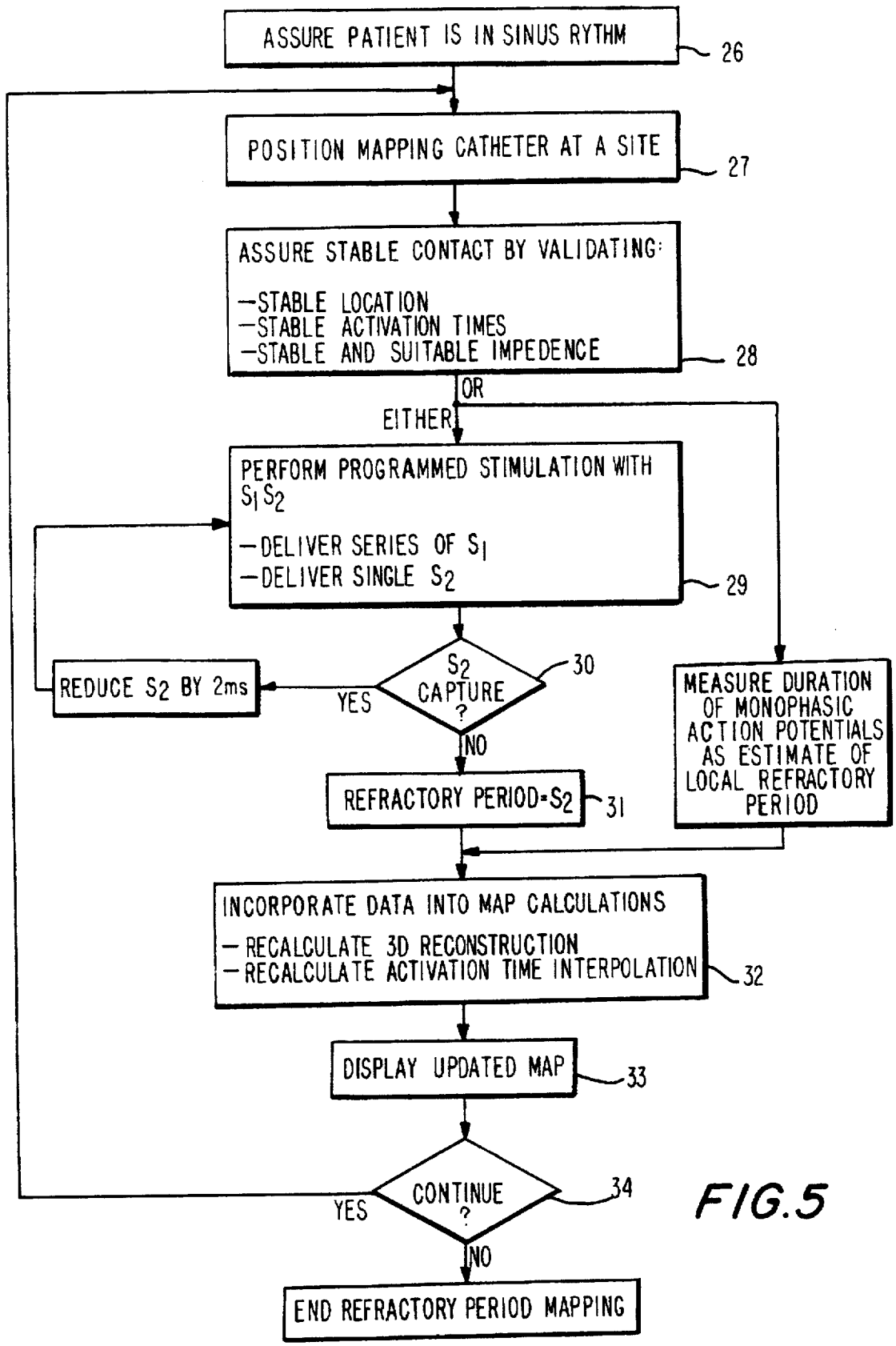
FIG. 5 is a flowchart showing the steps used in performing refractory period mapping.

FIG. 5 is a flowchart illustrating the steps followed in performing refractory period mapping 5. Again, the patient must be in a regular sinus rhythm 26, which can be achieved by cardioversion. The mapping catheter is moved to touch the endocardium of a site of the atria 27, and when stable contact is assured 28, an external stimulator delivers electrical stimuli to the endocardium in a programmed order 29 (a train of constant rate pacing followed by premature extra stimuli). This train of external pacing of the atria is repeated each time with a premature extra stimuli coupled at a shorter interval 30. The longest interval used for coupling the premature stimuli that does not cause local activation is termed the local refractory period 31. The information is recorded and incorporated into the map calculations 32, namely, a plurality of local refractory periods, is portrayed as the local refractory map of the atrium 33, and the process is continued until a map of sufficient detail is constructed 34. Alternatively, the local refractory period can be approximated by measuring the duration of the monophasic action potential (MAP) duration at each site 35. The data for the refractory period map may be collected at the same sites as for the activation map, by measuring the local activation time and the local refractory period in turn. Alternatively, the data for each map may also be collected at different sites.

Figure 6:
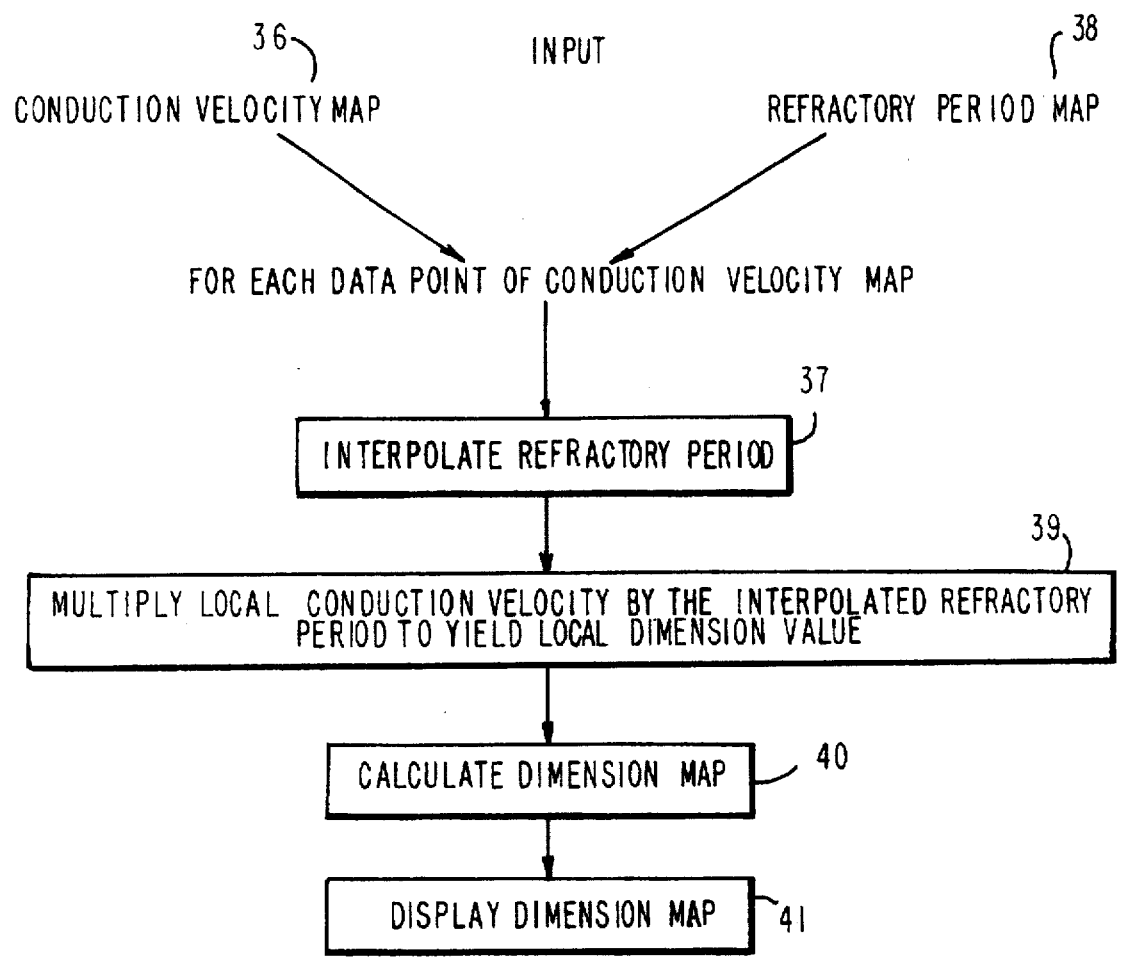
FIG. 6 is a flowchart describing the procedure used to calculate the dimension map.

The product of conduction velocity (mm/ms) times the refractory period (ms) results in the distance (mm) that a stimulating wave front must travel in a reentry circuit in order to travel the entire circuit always meeting the next cell just after the end of its refractory period i.e., when it is ready to be stimulated. To calculate the product of the previously acquired conduction velocity map times the refractory period map to obtain the dimension map 6 the procedure outlined in the flowchart of FIG. 6 is used. The local conduction velocity v can be multiplied by the refractory period value RP for each point on the conduction velocity map 39 to yield the local dimension value D, i.e., $D=v \times RP$, for each point. If two separate sets of sites were used to create the activation map and the refractory period map, then for each data point in the conduction velocity map 36, a corresponding refractory period value RP is calculated by interpolating between points 37 on the refractory period map 38. All the points D can then be displayed in a dimension map 40, which can be shown superimposed on the heart anatomy 41.

Once the activation map and the dimension map have been created, the information contained therein must be processed to calculate possible lines and/or points of ablation. Such calculations are related to an assumption that any electrical activation wavefront will spread on a path that is not tightly curved. Based upon experimental data, the minimum radius of curvature of an activation wavefront can be approximated by a, which is believed to be about 3 mm. A circle of a radius a can be defined such that the circumference X, where $X=2\pi a$, is the shortest circular path physically possible in the human heart. In the normal human heart, if the activation wavefront were to travel in such a circular path it would not create a reentrant circuit, since upon arriving at the beginning of the circle the next cell would still be in a state where it is unable to be stimulated (i.e., refractory), and the circular path of activation would be terminated. Even in circular paths with a radius much larger than a, the normal human heart cannot create reentrant circuits. In the heart of an AF patient, however, the conduction of the activation wavefront is usually much slower, and the wavefront may arrive at the tail of a circular path later than the refractory period of that site. Hence there exist many possible propagation circuits that could cause reentry, so long as the path that the wavefront has traveled is at least of length D, the local dimension value.

The design of the ablation lines and/or points according to this invention uses three criteria:

1. The minimum radius of curvature of a stimulation wavefront is a.
2. Any path closing a loop at a particular location in the heart must be of length D, the local dimension number, in order to cause the development of a reentrant conduction path.
3. The electrical continuity between the SA node and the AV node must be preserved.

These criteria may be implemented in a number of different algorithms that are designed to compute ablation lines that prevent the formation of reentry circuits in the tissue, and at the same time preserve the electrical continuity between the SA and AV node. An example of such an algorithm is outlined in the flowchart in FIG. 7. Given an input of the dimension map and the activation map superimposed on the atrial anatomy 50, critical areas such as fixed conduction blocks (caused by the entry of veins into the heart, scar tissue or other factors) 51, the SA node 52 and the AV node 53 can be identified. In this example algorithm the computing means starts at any one of the conduction blocks identified 54.

Possible ablation lines λ and Ψ are calculated 55 for each conduction block 56. Then, each ablation line is assumed to be a conduction block 57, and the process of calculating additional ablation lines is repeated 58. Once the possible sets of ablation lines have all been calculated 59, the length and number of ablation lines is optimized, for example, by determining the least number of ablation lines, the shortest ablation lines, the most easily generated ablation lines, or similar criteria. The ablation lines determined can be superimposed on a 3-D display of the anatomy 60.

Figure 7:
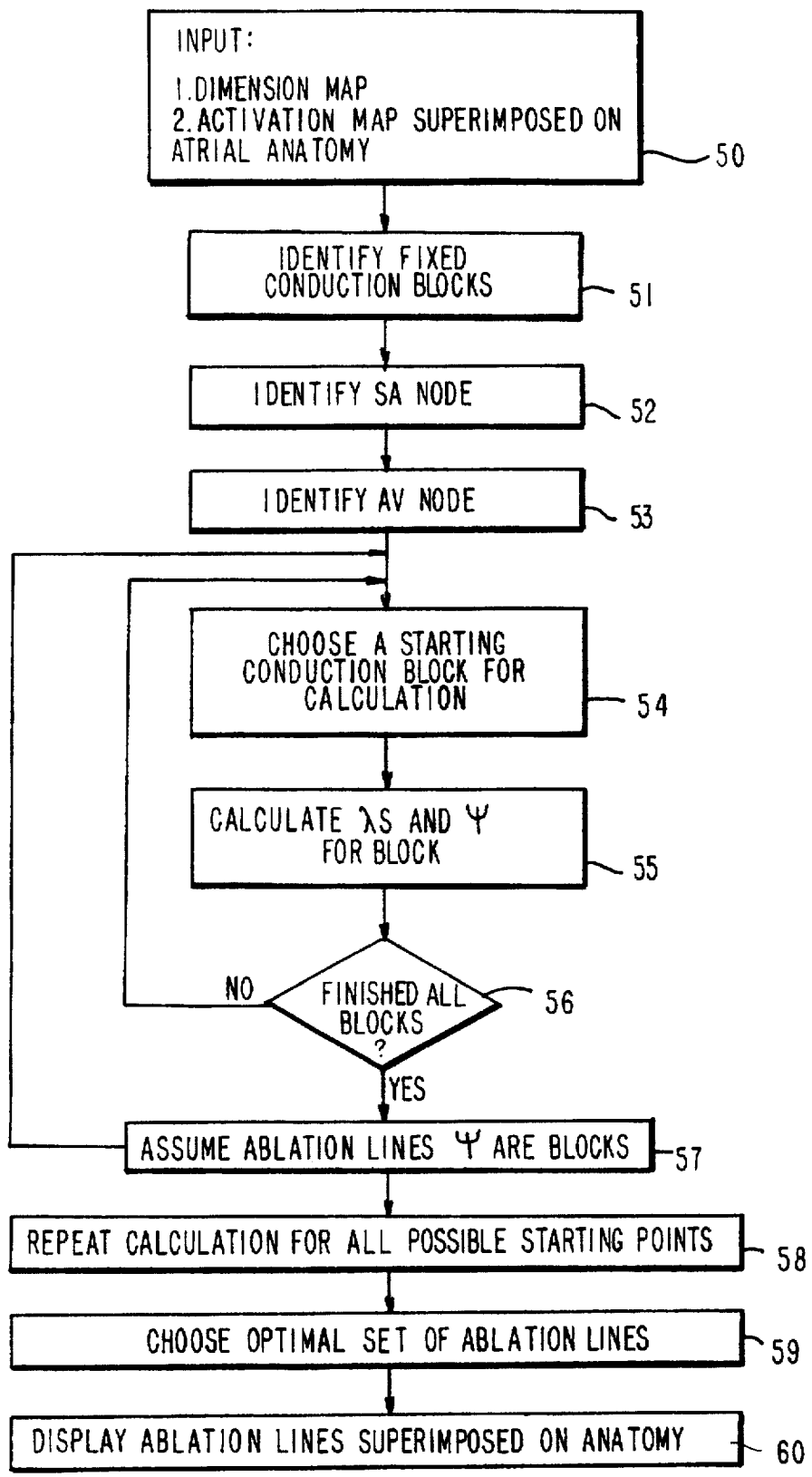
FIG. 7 is a flowchart depicting the procedure for designing the ablation lines.
Figure 8A:
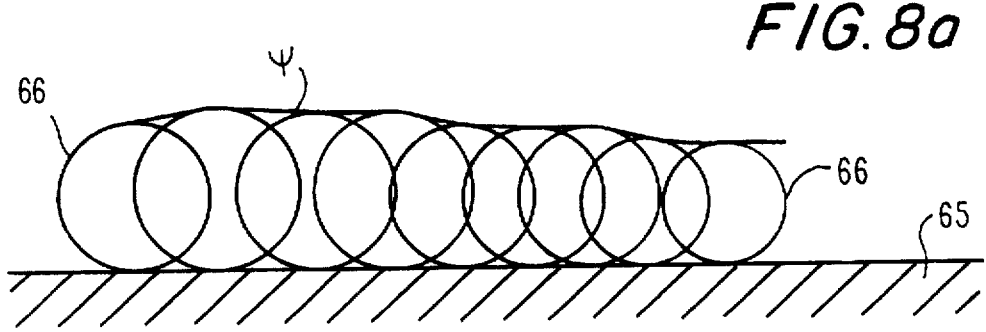
FIG. 8a represents circular reentrant circuits along a linear conduction block.
Figure 8B:
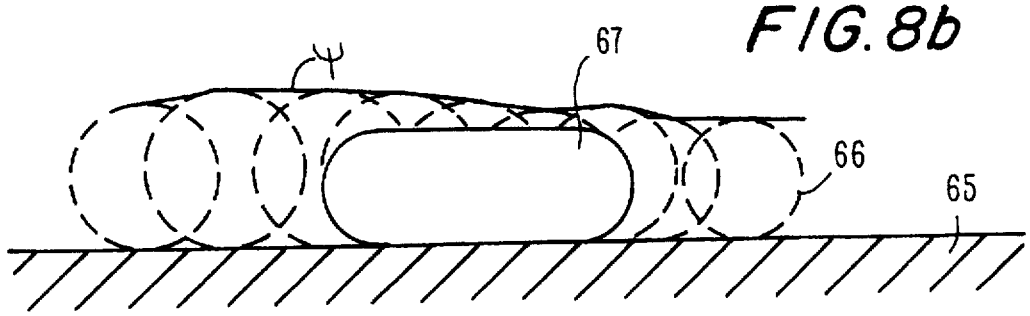
FIG. 8b shows how an oval-shaped reentrant circuit could form within an ablation line placed at the outer edge of possible circular reentrant paths along a linear conduction block.
Figure 8C:
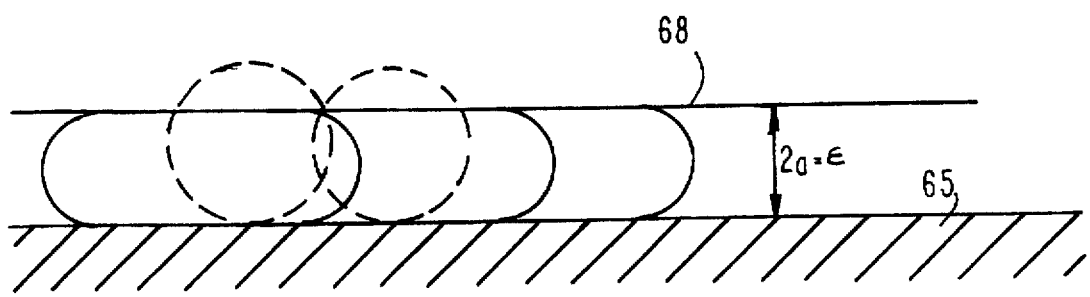
FIG. 8c depicts a possible ablation line at slightly less than 2a from the edge of a linear conduction block, which would prevent both circular and oval ablation lines from forming alongside the block.

Exemplary applications of the algorithm represented in FIG. 7 are described in FIGS. 8a–12b. For a theoretical linear conduction block 65, circular reentrant circuits 66 of length D could form along the edge of the block 65, as in FIG. 8a. The size of the circle at each point along the block 65 depends on the local value of D at each site. In this case a possible ablation line Ψ could be a line just inside the outermost edge of the circles. Since ablated tissue becomes a conduction block, this would prevent all circular circuits of length or circumference D or greater from forming. The circuits 67 could, however, be more oval in shape, as shown in FIG. 8b. Then, even after applying the ablation line shown in FIG. 8a, a reentrant pathway of length D could develop alongside the conduction block. In order to prevent the formation of both types of circuits, an ablation line could be placed along the outer edge of the most narrow oval-shaped pathways. Since the minimum turning radius of the pathway must be at least a, the narrowest oval shapes that might form are of width 2a. Then a possible ablation line 68 would be a small distance ε less than 2a from the boundary edge (FIG. 8c).

Figure 9A:
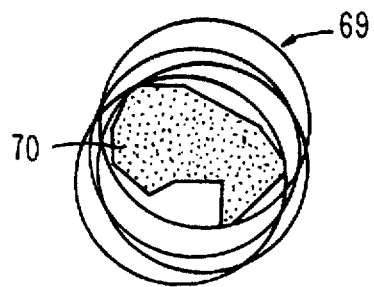
FIG. 9a represents possible circular reentrant circuits around an approximately circular conduction block.
Figure 9B:
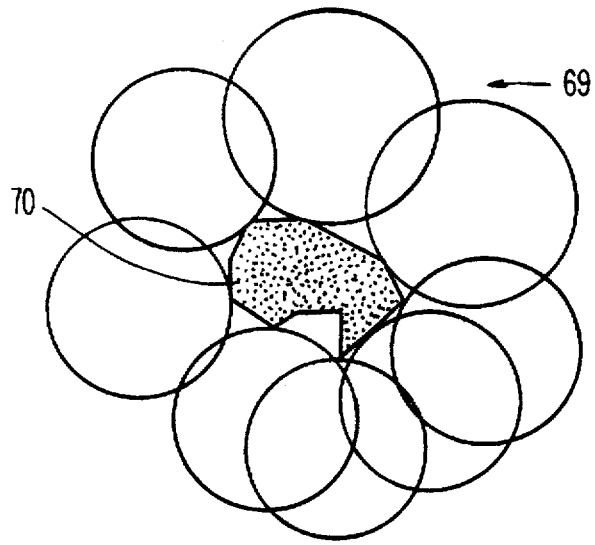
FIG. 9b depicts possible circular reentrant circuits along the edge of an approximately circular conduction block.
Figure 10:
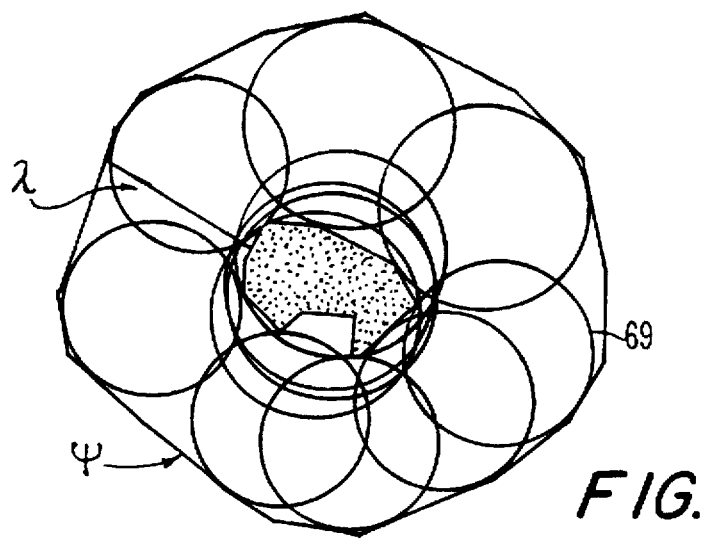
FIG. 10 shows possible ablation lines $\lambda$ and $\Psi$ that would prevent circular reentrant circuits of length D or longer from forming around or alongside an approximately circular conduction block.

In the case of an approximately circular conduction block, circular reentrant circuits 69 could form around the block 70 (FIG. 9a) or alongside it (FIG. 9b). Possible ablation lines that would prevent the formation of circular reentrant circuits 69 from forming around or alongside a circular conduction block 70 might be a line Ψ just inside the outer edge of the possible circuits alongside the block 70, and a line λ connecting this ablation line with the block 70 (FIG. 10).

Figure 11:
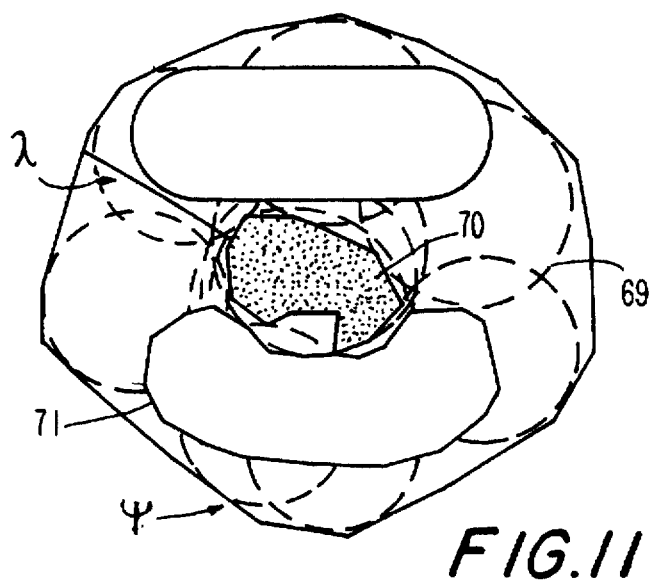
FIG. 11 shows how oval-shaped reentrant pathways of length D might form between the circular conduction block and the ablation lines $\lambda$ and $\Psi$.
Figure 12B:
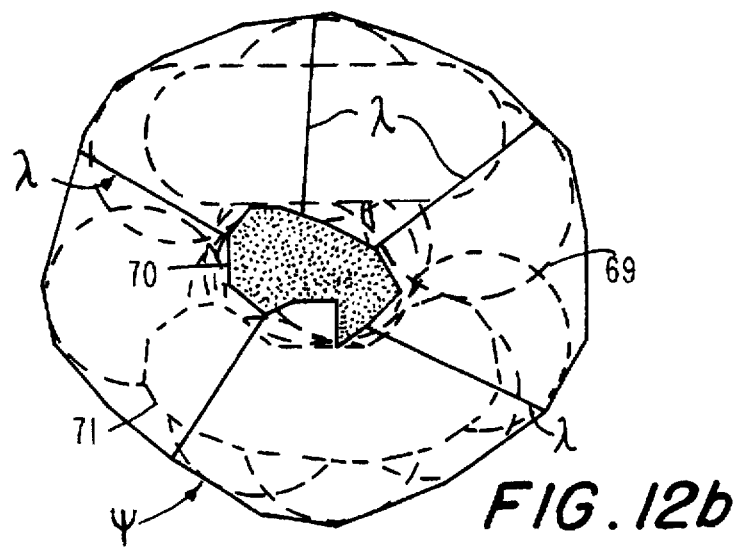
FIG. 12b shows how placing additional radial ablation lines of type $\lambda$ between the block and the ablation line $\Psi$ prevents reentrant circuits from forming alongside the conduction block because there is no area within $\Psi$ big enough to form a reentrant circuit of length D (with curvature no greater than a)
Figure 12A:
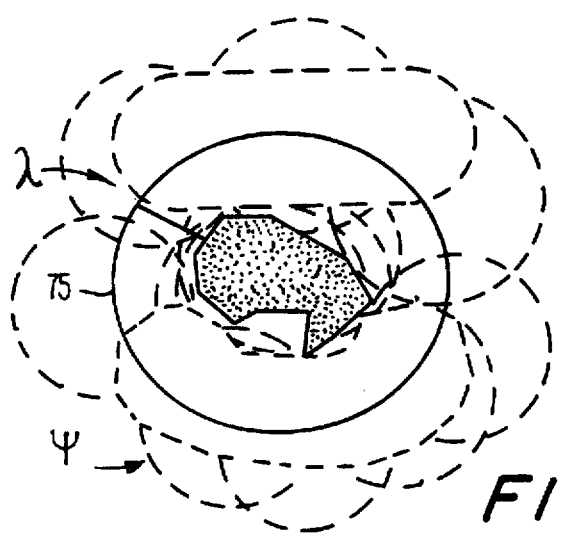

While line λ would prevent circuits of any shape forming around the conduction block within line Ψ, more oval reentrant circuits 71 might still develop between the ablation lines and the circular conduction block 70 (FIG. 11). Different algorithms might use different ablation lines to prevent these types of reentry circuits 71 from forming. Since the minimum radius of curvature of a stimulation wavefront is a, and the minimum width of an oval pathway is 2a as in the case with a linear conduction block, one possible solution would be to place an ablation line 75 a distance just less than 2a around the circular conduction block 70 (FIG. 12a). Another solution might be to add extra radial lines of type λ that would prevent reentry circuits from forming since there would remain no possible paths of length D (with curvature always equal to or less than a) within the tissue inside ablation line Ψ (FIG. 12b).

Figure 13:
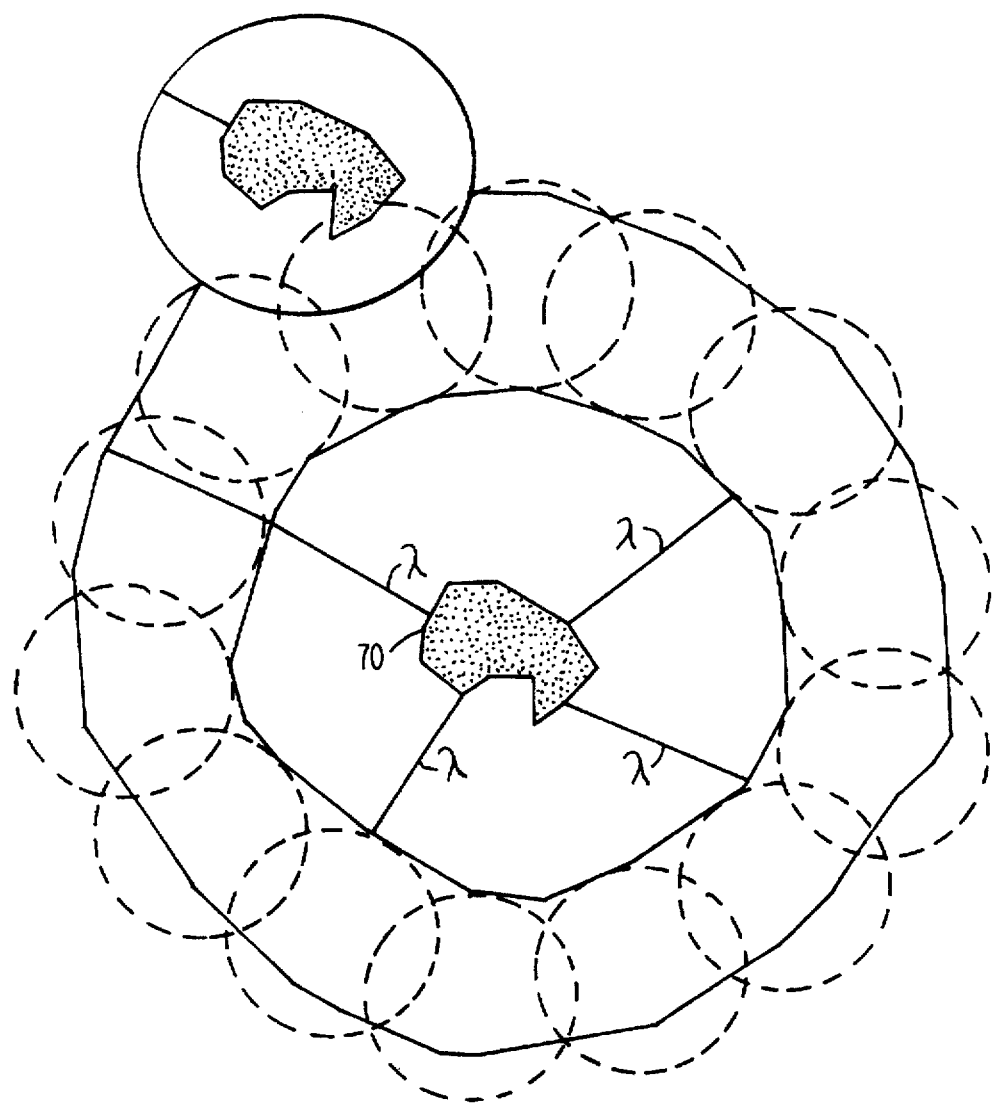
FIG. 13 shows that considering ablation line $\Psi$ as a circular conduction block and calculating ablation lines of type $\lambda$ and type $\Psi$ will prevent the formation of reentrant circuits around and alongside it. Other ablation lines may be used to optimize the suggested lines to a minimum total length.

In turn, the suggested ablation lines around and alongside each conduction block identified are calculated. The ablation lines of type Ψ are then taken into consideration in the calculations, since they can be considered conduction blocks (FIG. 13), and may be used to minimize the total length of the suggested ablation lines. The process is repeated until the entire area of the atria has been covered, and there is no area remaining in which a reentrant circuit could form.

The entire calculation is then repeated starting from a different conduction block, since the total length of the ablation lines suggested will differ depending on the starting point. After completing the entire calculation starting at each conduction block, the optimal set of suggested ablation lines (shortest/easiest to perform, or some other criteria) that conforms to the three design criteria listed above is chosen and displayed superimposed on the heart anatomy.

The computer generated boundary lines can be superimposed on the heart anatomy along with the location of the SA node, the AV node and the entrance of the blood vessels into the chamber. Since the catheter tip is continuously locatable, it can be superimposed on the display to guide the performance of the ablation procedure. The results of the mapping and ablation procedure are checked by performing another activation map procedure.

Real time locating of the mapping and ablating catheter tip can be achieved by several technologies. The advantage of using x-ray fluoroscopy for locating the tip of a cardiac catheter is based on the ease of performance using regular, available catheters. However, the resolution of this method is at best about 1 cm. Another disadvantage is that utilizing x-ray radiation for mapping procedures requires repeated transilluminations, thus increasing the exposure of the physician and the patient to the x-ray radiation.

In the last decade alternative methods have been developed for permanent portrayal of catheters during mapping procedures by making use of non-ionizing waves or fields, and these methods have the advantage of limiting the radiation exposure for the patients and the physician. These methods offer better quantitative, high resolution locating information than the location information offered by the x-ray radiation technique. Several technical realizations have been disclosed in U.S. Pat. No. 4,173,228 to Van Steenwyk, U.S. Pat. No. 4,697,595 to Breyer, U.S. Pat. No. 4,945,305, to Blood, and U.S. Pat. No. 5,042,486 to Pfeiler. Other possible embodiments of the means to find the real-time location of the catheter tip will be discussed below. The physical principle common to these non x-ray locating technologies is that they make use of a transmitter for electromagnetic or acoustic waves located at the tip of a catheter, these waves being acquired by a receiving antenna attached to, or disposed in or near the patient and being converted into electrical signals. The location of the catheter can then be superimposed on a heart chamber image disclosing wall architecture acquired by same or other means of imaging, or by reconstructing the surface formed by the plurality of endocardial points acquired during the mapping procedure. In an alternative embodiment, the catheter tip may be a receiving antenna, and the external antennas may be transmitting antennas.

For locating catheter tips by use of electromagnetic fields, marking of the catheter tip is achieved by an antenna disposed at the catheter tip, with an antenna feed guided in or along the catheter. An electrical antenna (dipole) or a magnetic antenna such as a magneto-resistor sensor, concentric coil, fluxgate magnetometer, Hall effect sensor, coils, etc., can be used. The antenna can be operated as a transmission antenna or as a reception antenna, with the extracorporeal antennas located outside of the patient's body correspondingly functioning as reception antennas or transmission antennas.

With the use of acoustic fields, locating the tip of the mapping/ablation catheter can be achieved either by using a piezo-electric element deposited in the lumen of the tip of the mapping/ablation catheter, or by a piezo-electric coating on the mapping/ablation catheter. The one or more reference catheters use the same configuration, i.e., either a piezo-electric crystal deposited in the tip or a coating on the tip. Each of the one or more reference catheters, as well as the mapping/ablation catheter, are used either as transmitting means for the acoustic field or as a receiving means for the same field. The method of locating the tip of the mapping/ablation catheter is based on defining the relative position of each catheter relative to the position of the one or more reference catheters that are left in a stable position during the mapping procedure. Relative location of all of the catheters is calculated as the triangulation of the distances measured from each of the catheters to the one or more reference catheters. Each catheter in its turn transmits an acoustic field, and the arrival time of this transmission at each of the one or more catheters, is recorded. Distances are calculated so that triangulation can be performed and the location of the mapping/ablation catheter relative to the fixed frame of the reference catheter or catheters, can be calculated. In some possible embodiments, references or reference catheters may be placed outside the body of the patient, for example, on the skin.

The sensor at the catheter tip is constructed with respect to the property to be sensed and the interaction with the locating field waves. For example, a metal electrode for conducting local electrical activity may interact with the locating technique using electromagnetic waves. This problem can be solved in the preferred embodiment by using composite material conductors. When the catheter tip is to be used to measure monophasic action potentials, the tip may be, for example, silver fluoride. In this case the signal amplification should be wide band DC and coupled.

The delivery port at the tip of the catheter is designed with respect to the energy characteristic to be delivered. In the present embodiment the delivery port is the sensing electrode and can function as an electrode for sensing electrical activity, as an antenna to deliver radio-frequency energy to perform ablation of tissue in close contact to the delivery port, or to deliver electrical stimuli for pacing the heart from that site.

In another embodiment of the invention a thermistor is incorporated within the catheter tip for measuring the tip temperature as a way for controlling the amount of energy delivered to the tissue.

The location, positioning, and sensing technology and the construction and use of sensing, reference, and ablation catheters, especially ablation catheters using RF or laser energy, to which reference is made above, is set forth in more detail in U.S. Pat. No. 5,391,199, co-pending U.S. patent application Ser. No. 08/293,859, filed Aug. 19, 1994, and PCT patent application Ser. No. PCT/US95/01103, filed Jan. 24, 1995, each of which is commonly assigned and each of which is incorporated herein by reference.

Figure 14:
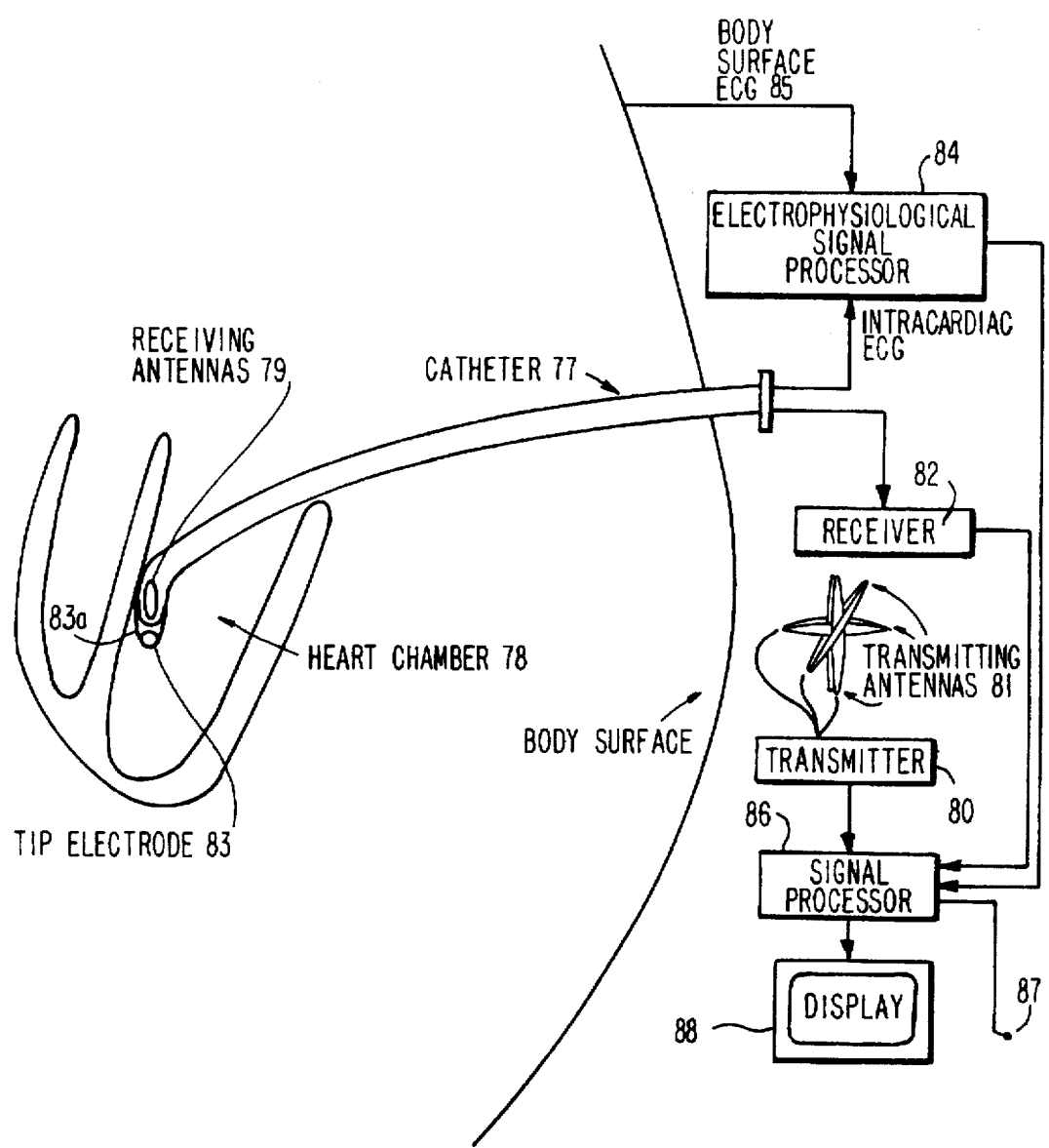
FIG. 14, describes a possible embodiment of an electromagnetic mapping/ablation catheter tip location system.

More specifically, a possible embodiment of the electromagnetic location system could be as that shown in FIG. 14. A catheter 77 is introduced into the heart chamber 78 in the body of a patient. The catheter has one or more, for example, from one to ten, receiving antennas 79 at its tip. Transmitting antennas 81 are supplied with energy by a transmitter 80. The transmitting antennas 81 may be, for example, a dipole or a coil. A receiver 82 is provided for locating the position of the tip. The receiver 82 receives the electromagnetic waves generated by the antenna 81 by means of a plurality of receiving antennas 79. An electrode 83 placed on the catheter tip 83a, receives local electrical activity of the heart chamber muscle. The signals from the electrode 83 are supplied to an electrophysiological signal processor 84 which calculates the local activation time delay by subtracting the absolute local activation time from the absolute reference time measured from the body surface electrogram 85, of the present heart cycle. The signals from the receiver 82 and the output of electrophysiological signal processor 84 are supplied to a signal processor 86 which constructs an image of the activation map.

Information regarding the heart chamber architecture is supplied to the signal processor via a separate input 87. The images are superimposed and are portrayed on the display 88.

To overcome the problems introduced by the repetitive heart movement of each cardiac cycle, the location information that is recorded is gated to a fixed point in the cardiac cycle. Therefore, anatomical maps of the studied chamber will be presented "frozen" and will correspond to the chamber geometry at a fiducial point in time of the cardiac cycle.

In an alternative embodiment the antennas 79 in the tip of the catheter 77 are transmitting antennas and the receiving antennas are located outside the body of the patient.

According to another alternative embodiment the transmitter and receiver may be an ultrasound transmitter or receiver instead of electromagnetically operating devices.

Figure 15:
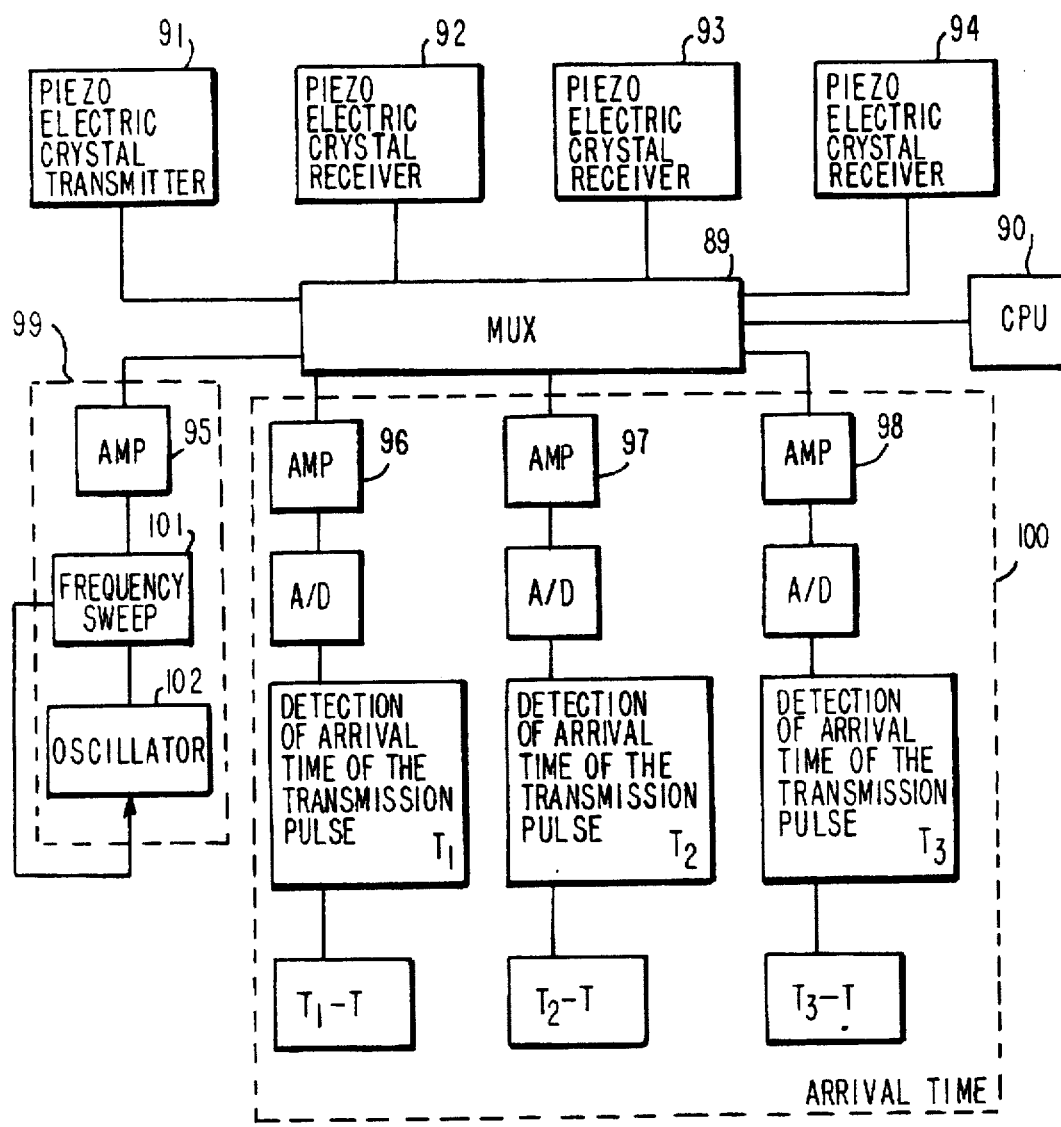
FIG. 15 describes a possible piezo-electric embodiment of a mapping/ablation catheter tip location system.

FIG. 15 describes the system for detection and location of the mapping/ablating catheter using a piezo-electric embodiment. In this particular example, three reference catheters are used. A multiplexer 89, driven by a Central Processing Unit (CPU) 90, controls the connection of each of the piezo-electric crystals 91, 92, 93 and 94 deposited in each of the four catheters, one of the catheters being the mapping/ablating catheter and the other three being the reference catheters. Included are four amplifiers 95, 96, 97 and 98, one of them 95 connected to the transmitting means 99 and the other three 96, 97 and 98 connected to the receiving means 100. The CPU 90 switches each of the catheters, sequentially, so that each in turn is connected to the transmitting means 99 and the rest are connected to the receiving means 100. The basic frequency of the CPU switching function can be programmed by the user and is usually set to be 1/10th of the basic frequency of operation of the piezo-electric crystals (between 40–80 KHZ). A transmitting means 99 is designed such that a linear frequency sweep device 101 drives the piezo-electric crystal via an amplifier 95. The oscillator 102 scans a pre-programmed frequency band at a CPU 90 controlled rate.

Figure 16:
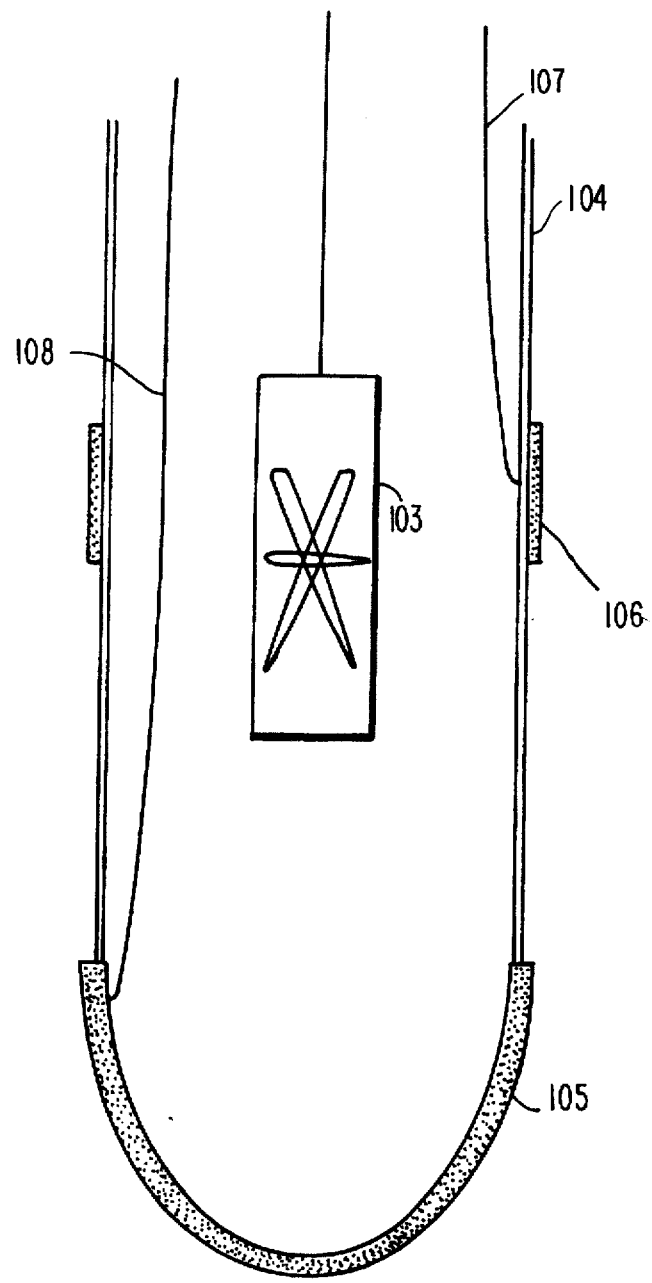
FIG. 16 describes a possible embodiment of a catheter tip designed to be used with an electromagnetic embodiment of the system.

FIG. 16 shows details of the catheter tip of a catheter designed for use with an electromagnetic embodiment of the system. The receiving antennas 103 are located near the catheter tip, inside sheath 104. The catheter has a tip electrode 105, and may have additional electrodes 106 that are electrically connected to conductors 107, 108 leading to the proximal end of the catheter.

Figure 17:
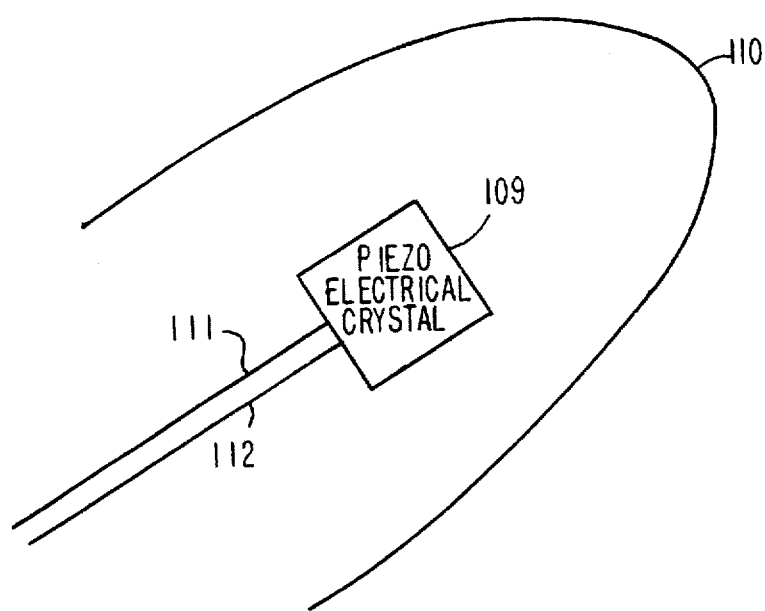
FIG. 17 describes one possible embodiment of a locatable catheter tip using a piezo-electric embodiment of the system.

FIG. 17 shows the details of the tip of a catheter designed to be used in a piezo-electric embodiment of the system. The piezo-electric crystal 109 is located inside the catheter tip 110 and two electrically conducting wires 111, 112 are receiving or transmitting electromagnetic signals to or from the piezo-electric crystal. In an alternative embodiment of the catheter tip 110 for use with a piezo-electric embodiment, a bio-compatible piezoelectric material can be disposed on the outer surface of the distal tip of the catheter, said coating being connected at separate points to two electrically conducting wires.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method for treating cardiac arrhythmias, which comprises the steps of:

(a) collecting local information concerning a patient's heart so as to determine a local dimension value characteristic of conduction in the heart tissue;

(b) analyzing said information to determine lines or points of ablation, wherein the information is analyzed to optimize the line or points of ablation, wherein the continuous or discontinuous ablation lines interrupt each possible geometric shape having a radius $\geq a$ and a circumference or outer perimeter greater than or equal to the dimension value at a given location; and (c) creating lines or points of ablation.

2. The method of claim 1, wherein in step (b) each geometric shape interrupted is circular or oval.

3. The method of claim 1, wherein the step of collecting local information concerning a patient's heart comprises the steps of:

(i) creating an activation map of the heart of a patient wherein a conduction velocity map is derived from the activation map;

(ii) creating a refractory period map of said heart; and (iii) creating a dimension map of said heart, wherein said dimension map is a mathematical product of the conduction velocity map and the refractory period map.

4. The method of claim 3, wherein in step (iii) the dimension map is created from the information gathered in steps (i) and (ii).

5. The method of claim 3, wherein the activation map is created by the steps comprising:

(a) positioning the distal tip of each of one or more catheters at a site within a patient's heart;

(b) sensing location information at each site;

(c) sensing local information at each site;

(d) processing sensed data from steps (b) and (c) to create one or more data points; and (e) repeating steps (a) to (d) one or more times to create sufficient data points for a map.

6. The method of claim 5, which comprises an additional step (f) of transmitting the data points from step (e) to a receiving means.

7. The method of claim 5, which comprises an additional step of deriving a conduction velocity map the activation map.

8. The method of claim 1, wherein the step of collecting local information concerning a patient's heart comprises the steps of:

(i) creating an activation map of at least a portion of a chamber of the heart wherein a conduction velocity map is derived from the activation map;

(ii) creating a refractory period map of said chamber or part thereof; and (iii) creating a dimension map of said chamber or part thereof, wherein said dimension map is a mathematical product of the conduction velocity map and the refractory period map.

9. The method of claim 8, which also comprises the step of obtaining a three-dimensional image of one or more chambers of the heart.

10. The method of claim 9, wherein the three-dimensional image of a chamber of the heart is reconstructed by the steps comprising:

(a) positioning the distal tip of each of one or more catheters at a site on the endocardium of a patient's heart chamber;

(b) sensing location information at each site;

(c) moving the distal tip of one or more catheters to a new site; and (d) repeating steps (a) to (c) one or more times to create sufficient data points for a reconstruction.

11. The method of claim 10, which comprises an additional step (e) of transmitting the data points from step (d) to a receiving means.

12. The method of claim 8, wherein in step (iii) the dimension map is created from the information gathered in steps (i) and (ii).

13. The method of claim 3 or 8, wherein a refractory period map is created by the steps comprising:

(a) positioning the distal tip of each of one or more catheters at a site on the endocardium of a patient's heart;

(b) sensing location information at each site;

(c) determining the refractory period at each site;

(d) processing sensed information from steps (b) and (c) to create one or more data points; and (e) repeating steps (a) to (d) one or more times to create sufficient data points for a refractory period map.

14. The method of claim 13, which comprises an additional step (f) of transmitting the data points from step (e) to a receiving means.

15. The method of claim 3 or 8, wherein a dimension map is created by the steps comprising:

(a) deriving a conduction velocity map;

(b) determining for a data point on the conduction velocity map of step (a) a corresponding refractory period value on the refractory period map;

(c) multiplying the conduction velocity value of the data point in step (b) by the corresponding refractory period value to calculate the local dimension value; and (d) repeating steps (b) and (c) one or more times to create sufficient data points for a dimension map.

16. The method of claim 15, which comprises an additional step (e) of transmitting the data points from step (d) to a receiving means.

17. The method of claim 10 or 5, wherein in step (b) the location information is measured relative to a reference catheter within the patient's body.

18. The method of claim 10, 5, or 7, wherein in step (b) the location information is measured relative to a reference outside the patient's body.

19. A method for determining lines or points of ablation to treat arrhythmias in the heart of a patient, which comprises the steps of:

(a) creating an activation map of the heart of a patient;

(b) creating a refractory period map of said heart;

(c) creating a dimension map of said heart; and (d) analyzing the dimension map of step (c) to determine lines or points of ablation.

20. The method of claim 19, wherein in step (c) the dimension map is created from the information gathered in steps (a) and (b).

21. A method for determining lines or points of ablation to treat arrhythmias in the heart of a patient, which comprises the steps of:

(a) creating an activation map of at least a part of a chamber of the patient's heart wherein a conduction velocity map is derived from the activation map;

(b) creating an refractory period map of said chamber or part thereof;

(c) creating a dimension map of said chamber or part thereof, wherein said dimension map is a mathematical product of the conduction velocity map and the refractory period map; and (d) analyzing the dimension map of step (c) to determine lines or points of ablation.

22. The method of claim 19, which comprises the additional step of deriving a conduction velocity map from the activation map created in step (a).

23. The method of claim 19 or 21, wherein a dimension map is created by the steps comprising:
- (a) deriving a conduction velocity map;
- (b) determining for a data point on the conduction velocity map of step (a) a corresponding refractory period value on the refractory period map;
- (c) multiplying the conduction velocity value of the data point in step (b) by the corresponding refractory period value to calculate the local dimension value; and
- (d) repeating steps (b) and (c) one or more times to create sufficient data points for a dimension map.

24. The method of claim 19 or 21, wherein a refractory period map is created by the steps comprising:
- (a) positioning the distal tip of each of one or more catheters at a site on the endocardium of a patient's heart;
- (b) sensing location information at each site;
- (c) determining the refractory period at each site;
- (d) processing sensed information from steps (b) and (c) to create one or more data points; and
- (e) repeating steps (a) to (d) one or more times to create sufficient data points for a refractory period map.

25. The method of claim 24, wherein in step (b) the location information is measured relative to a reference catheter within the patient's body.

26. The method of claim 24, wherein in step (b) the location information is measured relative to a reference outside the patient's body.

27. The method of claim 19 or 21, wherein the activation map is created by the steps comprising:
- (a) positioning the distal tip of each of one or more catheters at a site within a patient's heart;
- (b) sensing location information at each site;
- (c) sensing local information at each site;
- (d) processing sensed data from steps (b) and (c) to create one or more data points; and
- (e) repeating steps (a) to (d) one or more times to create sufficient data points for a map.

28. The method of claim 27, wherein in step (b) the location information is measured relative to a reference catheter within the patient's body.

29. The method of claim 27, wherein in step (b) the location information is measured relative to a reference outside the patient's body.

30. A method of determining lines or points of ablation to treat arrhythmias in the heart of a patient, which comprises the steps of:
- (a) positioning the distal tip of each of one or more catheters at a site within a chamber of a patient's heart;
- (b) sensing location and local information at the site;
- (c) processing sensed information from step (b) to create one or more activation mapping data points;
- (d) repeating steps (a), (b), and (c) one or more times to create sufficient data points for an activation map;
- (e) calculating conduction velocity data points from the data received in step (d) to create a conduction velocity map;
- (f) determining the refractory period at each site;
- (g) repeating steps (a), (b), and (f) one or more times to create sufficient data points for a refractory period map;
- (h) multiplying the conduction velocity value of a data point from step (e) by the corresponding refractory period value to calculate the local dimension value;
- (i) repeating step (h) one or more times to create sufficient data points for a dimension map;
- (j) analyzing the dimension map from step (i) to determine lines or points of ablation.

31. A method for determining areas of ablation to treat arrhythmias in the heart of a patient, which comprises the steps of:
- (a) positioning the distal tip of each of one or more catheters at a site within a chamber of the patient's heart;
- (b) sensing location information at each site;
- (c) sensing local information at each site;
- (d) sensing or determining the refractory period at each site;
- (e) processing sensed information from steps (b), (c), and (d) to create one or more data points;
- (f) repeating steps (a), (b), (c), (d), and (e) one or more times to create sufficient data points for an activation map and a refractory period map;
- (g) calculating conduction velocity data points from the data received in step (f) to create a conduction velocity map;
- (h) multiplying the conduction velocity value of a data point in step (g) by the corresponding refractory period value to calculate the local dimension value;
- (i) repeating step (h) one or more times to create sufficient data points for a dimension map; and
- (j) analyzing the activation map from step (f) and the dimension map from step (i) to determine lines or points of ablation.

32. The method of claim 31, comprising an additional step of determining a refractory period value on the refractory period map of step (f) corresponding to a data point on the conduction velocity map of step (9).

33. A method of creating a refractory period map of a patient's heart, which comprises the steps of:
- (a) positioning the distal tip of each of one or more catheters at a site on the endocardium of a patient's heart chamber;
- (b) sensing location information at each site;
- (c) determining the refractory period at each site;
- (d) processing sensed information from steps (b) and (c) to create one or more data points;
- (e) repeating steps (a) to (d) one or more times to create sufficient data points for a refractory period map; and
- (f) transmitting said data points from step (e) to a receiving means.

34. The method of claim 30, 31, or 33 wherein in step (b) the location information is measured relative to a reference catheter within the patient's body.

35. The method of claim 30, 31, or 33 wherein in step (b) the location information is measured relative to a reference outside the patient's body.

36. A method of creating a dimension map of a patient's heart which comprises:
- (a) deriving a conduction velocity map;
- (b) creating a refractory period map;

(c) multiplying the conduction velocity value of a data point in step (a) by the corresponding refractory period value to calculate a local dimension value; and (d) repeating step (c) one or more times to create sufficient data points for a dimension map.

37. The method of claim 36, which comprises an additional step of transmitting the data points from step (d) to a receiving means.

38. The method of claim 36, which comprises an additional step of determining a refractory period value corresponding to a data point on the conduction velocity map of step (a).

39. A method for determining lines or points of ablation to treat arrhythmias with no discrete target in the heart of a patient, which comprises the steps of:

(a) creating an activation map, wherein a conduction velocity map is derived from the activation map, and refractory period map of at least a part of a chamber of a patient's heart;

(b) creating a dimension map of said chamber or a part thereof; and (c) calculating lines or points of ablation according to the criteria that any path with a radius of curvature larger than a, a being the minimum radius of curvature naturally occurring in the human heart, closing a loop at a particular location in the heart must be of a length equal to or greater than the local dimension number, D, wherein D is the mathematical product of the refractory period at any site on the refractory period map and the local conduction velocity at a corresponding site on the conduction velocity map, to cause the development of a reentrant conduction path, and that the electrical continuity must be preserved.

40. The method of claim 39 for determining lines or points of ablation to treat atrial arrhythmias with no discrete target in the heart of a patient, which comprises the steps of:

(a) creating an activation map of at least a part of a chamber of a patient's heart;

(b) creating a dimension map of said chamber or part thereof;

(c) identifying the SA node;

(d) identifying the AV node;

(e) identifying all conduction blocks;

(f) calculating each continuous or discontinuous line necessary to interrupt each possible geometric shape having a radius of ≧a and a circumference ≧D, positioned around the outer perimeter of a conduction block;

(g) repeating step (f) for each additional conduction block while also treating a continuous or discontinuous line from step (f) as a conduction block and calculating each additional continuous or discontinuous line necessary to interrupt each geometric shape having a radius ≧a or a circumference ≧D, positioned contiguous to the continuous or discontinuous line from step (f);

(h) repeating steps (f) and (g) starting from each conduction block identified in step (e); and (i) choosing an optimal set of ablation lines or points wherein the length of the lines or the number of points is minimal or the ablation lines or points are easiest to perform and there is electrical continuity between the SA node and the AV node and no reentrant circuit of length ≧D and radius of curvature ≧a may form.

41. The method of claim 40, wherein each interrupted geometric shape is a circular or oval shape.

42. An apparatus for the treatment of cardiac arrhythmias which comprises: (a) means for collecting local information concerning a patient's heart so as to determine a local dimension value characteristic of conduction in the heart tissue;

(b) means for analyzing said information to determine lines or points of ablation, wherein said means further comprises means for optimizing the lines or points of ablation, wherein the continuous or discontinuous ablation lines interrupt each possible geometric shape having a radius ≧a and a circumference or outer perimeter greater than or equal to the dimension value at a given location; and (c) means for creating lines or points of ablation.

43. The apparatus of claim 42, wherein each interrupted geometric shape is a circular or oval shape.

44. The apparatus of claim 42, wherein the means for collecting local information comprises:

(i) means for creating an activation map of the heart of a patient, wherein a conduction velocity map is derived from the activation map;

(ii) means for creating a refractory period map of said heart; and (iii) means for creating a dimension map of said heart.

45. The apparatus of claim 44, wherein the means for creating a dimension map is further comprised of means for utilizing the information gathered with means (i) and (ii) and for producing a mathematical product of said information.

46. The apparatus of claim 44, wherein the activation map creation means comprises:

(a) means for positioning the distal tip of each of one or more catheters at a site within a patient's heart;

(b) means for sensing location information at each site;

(c) means for sensing local information at each site;

(d) means for processing sensed data to create one or more data points; and (e) means for repeating the sensing and processing one or more times to create sufficient data points for a map.

47. The apparatus of claim 46 also having means for transmitting the data points to a receiving means.

48. The apparatus of claim 44, wherein the refractory period map creation means comprises:

(a) means for positioning the distal tip of each of one or more catheters at a site on the endocardium of a patient's heart;

(b) means for sensing location information at each site;

(c) means for determining the refractory period at each site;

(d) means for processing the sensed information to create one or more data points; and (e) means for repeating the positioning, sensing, determining the refractory period, and processing one or more times to create sufficient data points for a refractory period map.

49. The apparatus of claim 48 also having means for transmitting the data points to a receiving means.

50. The apparatus of claim 42, wherein the means for collecting local information comprises:

(i) means for creating an activation map of at least a part of a chamber of the heart;

(ii) means for creating a refractory period map of said chamber or part thereof; and (iii) means for creating a dimension map of said chamber or part thereof.

51. The apparatus of claim 50, which also comprises means for obtaining a three-dimensional image of one or more chambers of the heart.

52. The apparatus of claim 51, wherein the three-dimensional image of a chamber of the heart is reconstructed by means comprising:
(a) means for positioning the distal tip of each of one or more catheters at a site on the endocardium of a patient's heart chamber;
(b) means for sensing location information at each site;
(c) means for moving the distal tip of one or more catheters to a new site; and
(d) means for repeating the positioning, sensing, and moving one or more times to create sufficient data points for a reconstruction.

53. The apparatus of claim 52 also having means for transmitting the data points to a receiving means.

54. The apparatus of claim 50, wherein the means for creating a dimension map is comprised of means for utilizing the information gathered with means (i) and (ii) and for producing a mathematical product of said information.

55. The apparatus of claim 50, wherein the refractory period map creation means comprises:
(a) means for positioning the distal tip of each of one or more catheters at a site on the endocardium of a patient's heart;
(b) means for sensing location information at each site;
(c) means for determining the refractory period at each site;
(d) means for processing the sensed information to create one or more data points; and
(e) means for repeating the positioning, sensing, determining the refractory period, and processing one or more times to create sufficient data points for a refractory period map.

56. The apparatus of claim 44 or 50, wherein the dimension map creation means comprises:
(a) means for deriving a conduction velocity map;
(b) means for determining for a data point on the conduction velocity map a corresponding refractory period value on the refractory period map;
(c) means for multiplying the conduction velocity value of the data point by the corresponding refractory period value to calculate the local dimension value; and
(d) means for repeating the data point determination and multiplication one or more times to create sufficient data points for a dimension map.

57. The apparatus of claim 56 also having means for transmitting the data points to a receiving means.

58. The apparatus of claim 52, 46, 48 or 55, wherein said means for sensing measures location information relative to a reference catheter within a patient's body.

59. An apparatus for the treatment of cardiac arrhythmias in a patient's heart, wherein the cardiac arrhythmias have no focus, which comprises:
(a) means assuring that the heart is in a regular sinus rhythm by cardioverting the patient;
(b) a collector for collecting local information concerning a patient's heart at a plurality of data points, wherein said information is updated after the acquisition of each data point;
(c) an analyzer for analyzing said information to determine lines or points of ablation; and
(d) means for creating lines or points of ablation.

60. The apparatus of claim 52, 46 or 59, wherein said means for sensing measures location information relative to a reference catheter within the patient's body.

61. An apparatus for determining lines or points of ablation to treat arrhythmias in the heart of a patient, which comprises:
(a) means for creating an activation map of the heart of a patient;
(b) means for creating a refractory period map of said heart;
(c) means for creating a dimension map of said heart; and
(d) means for analyzing the dimension map to determine lines or points of ablation.

62. The apparatus of claim 61, wherein the means for creating a dimension map is further comprised of means for utilizing the information gathered with means (a) and (b) and for producing a mathematical product of said information.

63. An apparatus for determining lines or points of ablation to treat arrhythmias in the heart of a patient, which comprises:
(a) means for creating an activation map of at least a part of a chamber of the patient's heart, wherein a conduction velocity map is derived from the activation map;
(b) means for creating an refractory period map of said chamber or part thereof;
(c) means for creating a dimension map of said chamber or part thereof; and
(d) means for analyzing the dimension map to determine lines or points of ablation.

64. The apparatus of claim 61 or 63, wherein the activation map creation means comprises:
(a) means for positioning the distal tip of each of one or more catheters at a site within a patient's heart;
(b) means for sensing location information at each site;
(c) means for sensing local information at each site;
(d) means for processing sensed data to create one or more data points; and
(e) means for repeating the positioning, sensing, and processing one or more times to create sufficient data points for a map.

65. The apparatus of claim 64, wherein said means for sensing measures location information relative to a reference catheter within the patient's body.

66. The apparatus of claim 64, wherein said means for sensing measures location information relative to a reference catheter within the patient's body.

67. The apparatus of claim 61 or 63, wherein the refractory period map creation means comprises:
(a) means for positioning the distal tip of each of one or more catheters at a site on the endocardium of a patient's heart;
(b) means for sensing location information at each site;
(c) means for determining the refractory period at each site;
(d) means for processing sensed information to create one or more data points; and
(e) means for repeating the positioning, sensing, and processing one or more times to create sufficient data points for a refractory period map.

68. The apparatus of claim 67, wherein said means for sensing measures location information relative to a reference catheter within the patient's body.

69. The apparatus of claim 67, wherein said means for sensing measures location information relative to a reference catheter within the patient's body.

70. The apparatus of claim 61 or 63, wherein the dimension map creation means comprises:
   (a) means for deriving a conduction velocity map;
   (b) means for determining for a data point on the conduction velocity map a corresponding refractory period value on the refractory period map;
   (c) means for multiplying the conduction velocity value of the data point by the corresponding refractory period value to calculate the local dimension value; and
   (d) means for repeating the refractory period determination and multiplication one or more times to create sufficient data points for a dimension map.

71. An apparatus for determining lines or points of ablation to treat arrhythmias in the heart of a patient, which comprises:
   (a) means for positioning the distal tip of each of one or more catheters at a site within a chamber of a patient's heart;
   (b) means for sensing location and local information at the site;
   (c) means for processing sensed information from step (b) to create one or more activation mapping data points;
   (d) means for repeating the positioning, sensing, and processing one or more times to create sufficient data points for an activation map;
   (e) means for calculating conduction velocity data points from the data received to create a conduction velocity map;
   (f) means for determining the refractory period at each site;
   (g) means for repeating the positioning, sensing, and refractory period determination one or more times to create sufficient data points for a refractory period map;
   (h) means for multiplying the conduction velocity value of a data point by the corresponding refractory period value to calculate the local dimension value;
   (i) means for repeating the calculation of the local dimension value one or more times to create sufficient data points for a dimension map; and
   (j) means for analyzing the dimension map to determine lines or points of ablation.

72. An apparatus for creating a refractory period map of a patient's heart, which comprises:
   (a) means for positioning the distal tip of each of one or more catheters at a site on the endocardium of a patient's heart chamber;
   (b) means for sensing location information at each site;
   (c) means for determining the refractory period at each site;
   (d) means for processing sensed information to create one or more data points;
   (e) means for repeating the positioning, sensing, refractory period determination, and processing one or more times to create sufficient data points for a refractory period map; and
   (f) means for transmitting said data points to a receiving means.

73. An apparatus for determining areas of ablation to treat arrhythmias in the heart of a patient, which comprises:
   (a) means for positioning the distal tip of each of one or more catheters at a site within a chamber of the patient's heart;
   (b) means for sensing location information at each site;
   (c) means for sensing local information at each site;
   (d) means for sensing or determining the refractory period at each site;
   (e) means for processing sensed information to create one or more data points;
   (f) means for repeating the positioning, sensing, and processing one or more times to create sufficient data points for an activation map and a refractory period map;
   (g) means for calculating conduction velocity data points from the data received to create a conduction velocity map;
   (h) means for multiplying the conduction velocity value of a data point by the corresponding refractory period value to calculate the local dimension value;
   (i) means for repeating the calculation of the local dimension value one or more times to create sufficient data points for a dimension map; and
   (j) means for analyzing the activation map and the dimension map to determine lines or points of ablation.

74. The apparatus of claim 73 also having means for determining a corresponding refractory period value on the refractory period map for a data point on the conduction velocity map.

75. The apparatus of claim 71, 73 or 72, wherein said means for sensing measures location information relative to a reference catheter within a patient's body.

76. The apparatus of claim 71, 73 or 72, wherein said means for sensing measures location information relative to a reference catheter within the patient's body.

77. An apparatus for creating a dimension map of a patient's heart which comprises:
   (a) means for deriving a conduction velocity map;
   (b) means for creating a refractory period map;
   (c) means for multiplying the conduction velocity value of a data point on the conduction velocity map by the corresponding refractory period value to calculate a local dimension value; and
   (d) means for repeating said multiplication one or more times to create sufficient data points for a dimension map.

78. The apparatus of claim 77 also having means for transmitting the data points to a receiving means.

79. The apparatus of claim 77 also having means for determining a corresponding refractory period value for a data point on the conduction velocity map.

80. An apparatus for determining lines or points of ablation to treat arrhythmias with no discrete target in the heart of a patient, which comprises:
   (a) means for creating an activation map, wherein a conduction velocity map is derived from the activation map, and refractory period map of at least a part of a chamber of a patient's heart;
   (b) means for creating a dimension map of said chamber or a part thereof; and
   (c) means for calculating lines or points of ablation according to the criteria that any path with a radius of curvature larger than a, a being the minimum radius of curvature naturally occurring in the human heart, closing a loop at a particular location in the heart must be of a length equal to or greater than the local dimension number, D, wherein D is the mathematical product of the refractory period at any site on the refractory period map and the local conduction velocity at a corresponding site on the conduction velocity map, to cause the development of a reentrant conduction path, and that the electrical continuity must be preserved.

81. The apparatus of claim 80 for determining lines or points of ablation to treat atrial arrhythmias with no discrete target in the heart of a patient, which comprises:

(a) means for creating an activation map of all or part of a chamber of a patient's heart;

(b) means for creating a dimension map of said chamber or part thereof;

(c) means for identifying the SA node;

(d) means for identifying the AV node;

(e) means for identifying all conduction blocks;

(f) means for calculating each continuous or discontinuous line necessary to interrupt each possible geometric shape having a radius of $\geq a$ and a circumference $\geq D$, positioned around or alongside the outer perimeter of a conduction block;

(g) means for repeating the calculation of such a continuous or discontinuous line for each additional conduction block while also treating a prior continuous or discontinuous line as a conduction block and calculating each additional continuous or discontinuous line necessary to interrupt each geometric shape having a radius $\geq a$ or a circumference $\geq D$, positioned contiguous to the continuous or discontinuous line;

(h) means for repeating said calculation starting from each conduction block identified; and (i) means for choosing an optimal set of ablation lines or points wherein the length of the lines and/or the number of points is minimal or the ablation lines or points are easiest to perform and there is electrical continuity between the SA node and the AV node and no reentrant circuit of length $\geq D$ and radius of curvature $\geq a$ may form.

82. The apparatus of claim 81, wherein each interrupted geometric shape is a circular or oval shape.

83. A method for treating cardiac arrhythmias in a patient's heart, wherein the cardiac arrhythmias have no focus, which comprises the steps of:

(a) assuring that the heart is in a regular sinus rhythm by cardioverting the patient;

(b) collecting local information concerning the patient's heart, at a plurality of data points, wherein said information is updated after the acquisition of each data point;

(c) analyzing said information to determine lines or points of ablation; and (d) creating lines or points of ablation.

84. The method for treating cardiac arrhythmias of claim 83, wherein in step (b) anatomical obstacles to propagation of electrical activation are recorded as locations that are not associated with local electrical activity.

85. The method of claim 84, wherein the means for creating lines or points of ablation is entered into the patient's heart percutaneously.

86. The method of claim 83, wherein in step (d) the lines or points of ablation are created percutaneously.

87. The apparatus of claim 59, wherein anatomical obstacles to propagation of electrical activation are recorded as locations that are not associated with local electrical activity.

* * * * *